(12) United States Patent
Zeng et al.

(10) Patent No.: US 7,113,876 B2
(45) Date of Patent: Sep. 26, 2006

(54) TECHNIQUE AND ELECTRONIC CIRCUITRY FOR QUANTIFYING A TRANSIENT SIGNAL USING THRESHOLD-CROSSING COUNTING TO TRACK SIGNAL AMPLITUDE

(75) Inventors: Kefeng Zeng, State College, PA (US); Keat G. Ong, State College, PA (US); Craig A. Grimes, Boalsburg, PA (US)

(73) Assignee: SenTech Biomed Corporation, State College, PA (US)

( * ) Notice: Subject to any disclaimer, the term of this patent is extended or adjusted under 35 U.S.C. 154(b) by 81 days.

(21) Appl. No.: 10/936,125

(22) Filed: Sep. 8, 2004

(65) Prior Publication Data

US 2006/0064259 A1    Mar. 23, 2006

(51) Int. Cl.
G01R 13/00 (2006.01)
G01N 11/00 (2006.01)

(52) U.S. Cl. .................. 702/66; 702/54; 702/56; 702/78; 324/236; 324/239; 73/54.24; 73/64.53

(58) Field of Classification Search .............. None
See application file for complete search history.

(56) References Cited

U.S. PATENT DOCUMENTS

| | | | | |
|---|---|---|---|---|
| 5,295,084 | A * | 3/1994 | Arunachalam et al. | 702/50 |
| 6,359,444 | B1 | 3/2002 | Grimes | 324/633 |
| 6,393,921 | B1 | 5/2002 | Grimes et al. | 73/728 |
| 6,397,661 | B1 | 6/2002 | Grimes et al. | 73/24.06 |
| 6,639,402 | B1 | 10/2003 | Grimes et al. | 324/239 |
| 6,688,162 | B1 | 2/2004 | Bachas et al. | 73/64.42 |

OTHER PUBLICATIONS

K. Zeng, K.G. Ong, C. Mungle, and C A. Grimes, Rev. Sci. Instruments vol. 73, 4375-4380 (Dec. 2002).

H Reindl et al. "*Theory and Application of Passive SAW Radio Transponders as Sensors*," IEEE Transactions on Ultrasonics, Ferroelectrics, and Frequency Control, vol. 45, No. 5, (Sep. 1998).

(Continued)

*Primary Examiner*—Marc S. Hoff
*Assistant Examiner*—Manuel L Barbee
(74) *Attorney, Agent, or Firm*—Macheledt Bales & Heidmiller LLP

(57) ABSTRACT

Circuitry adapted for carrying out associated techniques for: (a) calculating a damping factor, e.g., a damping ratio represented by $\zeta$, or a quality factor Q, where $\zeta \approx 1/2Q$, for a transient signal received, having been emitted from a resonator-type sensor element; (b) determining amplitude, A, of the transient signal; or (c) generating a frequency response dataset of interrelated points for the transient signal. A threshold comparison circuit is included for converting the transient signal received into a first and second digital waveform; the first digital waveform represents cycle crossings of the transient signal associated with a first threshold value, and the second digital waveform represents cycle crossings of the transient signal associated with a second threshold value. The transient signal may be converted, likewise, into third, and so on, digital waveforms, whereby the third digital waveform represents cycle crossings of the transient signal associated with a third threshold value. Respective digital counters are included, each of which is adapted for determining a total number of cycles of the first, second, third, and so on, digital waveform. A processing unit of suitable speed and capacity is employed for the calculating of the damping factor, determining an amplitude, and/or generating a frequency response dataset.

34 Claims, 10 Drawing Sheets

OTHER PUBLICATIONS

Grimes, C.A., K.G. Ong, et al. "*Magnetoelastic sensors for remote query environmental monitoring*," Journal of Smart Materials and Structures, vol. 8, (1999) 639-646.

Jain, M.K., C. A. Grimes, "*A Wireless Magnetoelastic Micro-Sensor Array for Simultaneous Measurement of Temperature and Pressure,*" IEEE Transactions on Magnetics, vol. 37, No. 4, pp. 2022-2024, 2001.

* cited by examiner

TECHNIQUE AND ELECTRONIC CIRCUITRY FOR QUANTIFYING A TRANSIENT SIGNAL USING THRESHOLD-CROSSING COUNTING TO TRACK SIGNAL AMPLITUDE

BACKGROUND OF THE INVENTION

Field of the Invention

In general, the present invention relates to techniques for characterizing emissions from resonator-type sensor elements such as magnetoelastic resonant sensor elements, quartz crystal microbalance (QCM) elements, piezoelectric acoustic wave elements, etc.—to gain useful information from the sensor elements about an environment, analyte or sample of interest. These resonator-type elements each vibrate in response to sine wave excitation and impulse excitation. More-particularly, the invention is directed to unique circuitry adapted for carrying out associated unique techniques for: (a) calculating a damping factor, e.g., a damping ratio represented by $\zeta$, or a quality factor Q which is related to a damping ratio, $\zeta \approx 1/2Q$, for a transient signal received, having been emitted from a resonator-type sensor element; (b) determining amplitude, A, of the transient signal; or (c) generating a frequency response dataset of interrelated points for the transient signal.

A threshold comparison circuit is included in the circuitry for converting the transient signal received into a first and second digital waveform; the first digital waveform represents cycle crossings of the transient signal associated with a first threshold value, and the second digital waveform represents cycle crossings of the transient signal associated with a second threshold value. The transient signal may be converted, likewise, into third, fourth, and so on, digital waveforms, whereby the third digital waveform represents cycle crossings of the transient signal associated with a third threshold value, the fourth digital waveform represents cycle crossings of the transient signal associated with a fourth threshold value, and so on. Respective digital counters are included, each of which is adapted for determining a total number of cycles of the first, second, third, fourth, and so on, digital waveform. A processing unit of suitable speed and capacity is employed for calculating the damping factor, determining an amplitude, and/or generating a frequency response dataset-according to the invention.

General Discussion of Technological Areas, Provided by Way of Reference, Only

I. Excitation of resonator-type sensing elements

In earlier patented work, one of which is entitled "Magnetoelastic Sensor for Characterizing Properties of Thin-film/Coatings" U.S. Pat. No. 6,688,162, one or more of the applicants hereof detail the excitation of mangetostrictive/magnetoelastic elements, in operation as sensing units:

When a sample of magnetoelastic material is exposed to an alternating magnetic field, it starts to vibrate. This external time-varying magnetic field can be a time-harmonic signal or a non-uniform field pulse (or several such pulses transmitted randomly or periodically). If furthermore a steady DC magnetic field is superimposed to the comparatively small AC magnetic field, these vibrations occur in a harmonic fashion, leading to the excitation of harmonic acoustic waves inside the sample. The mechanical oscillations cause a magnetic flux change in the material due to the inverse magnetoelastic effect. These flux changes, in unison with the mechanical vibrations, can be detected in a set of EM emission pick-up coils. The vibrations of the sample are largest if the frequency of the exciting field coincides with the characteristic acoustic resonant frequency of the sample. Thus, the magnetoelastic resonance frequency detectable by an EM pick-up coil coincides with the frequency of the acoustic resonance. And, sensor element emissions can be detected acoustically, for example by a remote microphone/hydrophone or a piezoelectric crystal, by detecting the acoustic wave generated from the mechanical vibrations of the sensor. A relative-maximum response of the emissions remotely measured is identified to determine the sensing element's characteristic resonant frequency. The emissions from a sensing element of the invention can also be monitored optically whereby amplitude modulation of a laser beam reflected from the sensor surface is detected. Signal processing of the sensor elements can take place in the frequency-domain or in the time-domain using a field-pulse excitation.

FIG. 1A schematically depicts components of an apparatus and method of the invention for remote query of a thin-film layer or coating 14 atop a base magnetostrictive element 12. A time-varying magnetic field 17 is applied to sensor element 10, with a layer/coating 14 of interest having been deposited onto a surface of the base 14, by way of a suitable drive coil 16 such that emissions 19 from the sensor element can be picked-up by a suitable pick-up coil 18. Two useful ways to measure the frequency spectrum include: frequency domain measurement and the time domain measurement. In the frequency domain measurement, the sensing element's vibration is excited by an alternating magnetic field of a monochromatic frequency. The amplitude of the sensor response is then registered while sweeping ('listening') over a range of frequencies that includes the resonance frequency of the sensor element. Finding the maximum amplitude of the sensor response leads to the characteristic resonant frequency. FIG. 1B graphically depicts interrogation field transmissions from a drive coil (SEND) in both the frequency domain 22 and in the time-domain 26 (an impulse of, say, 200 A/m and 8 μs in duration). The transient response (emissions) captured 27 is converted to frequency domain 28 using a FFT to identify a resonant frequency.

II. Applications of resonator-type sensing elements

U.S. Pat. No. 6,688,162, issued 10 Feb. 2004 to Bachas, et al. in which the above passage appears, is hereby incorporated herein by reference for its further technological background discussion concerning the operation of resonator-type sensor elements in connection with direct quantitative measurement of parameters and characteristics of an analyte of interest, especially one in the form of a thin film/layer atop a surface of the element. Other patents—as well as published manuscripts—sharing at least one applicant hereof and containing technical background as to application(s) of resonator-type sensing elements in sensing an environment, itself, and/or the presence, concentration, chemical make up, and so on, of an analyte of interest (e.g., toxins or other undesirable chemical or substance, etc.) include: U.S. Pat. No. 6,639,402 issued 28 Oct. 2003 to Grimes et al. entitled "Temperature, Stress, and Corrosive Sensing Apparatus Utilizing Harmonic Response of Magnetically Soft Sensor Element(s);" U.S. Pat. No. 6,393,921 B1 issued 28 May 2002 to Grimes et al. entitled *"Magnetoelastic Sensing Apparatus and Method for Remote Pressure Query of an Environment;"* U.S. Pat. No. 6,397,661 B1 issued 4 Jun. 2002 to Grimes et al. entitled *"Remote Magneto-elastic*

*Analyte, Viscosity and Temperature Sensing Apparatus and Associated Method of Sensing;*" Reindl et al. "*Theory and Application of Passive SAW Radio Transponders as Sensors,*" IEEE Transactions on Ultrasonics, Ferroelectrics, and Frequency Control, vol. 45, no. 5, (September 1998); Grimes, C. A., K. G. Ong, et al. "*Magnetoelastic sensors for remote query environmental monitoring,*" Journal of Smart Materials and Structures, vol. 8 (1999) 639–646; and Jain, M. K., C. A. Grimes, "*A Wireless Magnetoelastic Micro-Sensor Array for Simultaneous Measurement of Temperature and Pressure,*" IEEE Transactions on Magnetics, vol. 37, No. 4, pp. 2022–2024, 2001.

III. Digital computers

A processor is the set of logic devices/circuitry that responds to and processes instructions to drive a computerized device. The central processing unit (CPU) is considered the computing part of a digital or other type of computerized system. Often referred to simply as a processor, a CPU is made up of the control unit, program sequencer, and an arithmetic logic unit (ALU)—a high-speed circuit that does calculating and comparing. Numbers are transferred from memory into the ALU for calculation, and the results are sent back into memory. Alphanumeric data is sent from memory into the ALU for comparing. The CPUs of a computer may be contained on a single 'chip', often referred to as microprocessors because of their tiny physical size. As is well known, the basic elements of a simple computer include a CPU, clock and main memory; whereas a complete computer system requires the addition of control units, input, output and storage devices, as well as an operating system. The tiny devices referred to as 'microprocessors' typically contain the processing components of a CPU as integrated circuitry, along with associated bus interface. A microcontroller typically incorporates one or more microprocessor, memory, and I/O circuits as an integrated circuit (IC). Computer instruction(s) are used to trigger computations carried out by the CPU. Frequency counters are digital indicating meters for measurement and display of input signals in the form of square wave(s) and pulse(s). Binary counters are digital circuits that have a clock input and one or more count output; the count output may give the number of clock cycles for a clock input, or may be employed to count pulses for an input digital waveform.

IV. Microelectronics—Structures and Devices

Microelectronics is that area of electronics technology associated with the fabrication of electronic systems or subsystems using extremely small (microcircuit-level) components. Semiconductor fabrication and processing is driven by the computer-electronics industry. The demands for greater capability and faster data collection and processing of smaller-sized computerized units result in a demand for smaller-and-smaller integrated circuit (IC) microcircuits. "Chip" and/or 'microchip' are often used to refer to any one or interrelated operational set of micro-miniaturized, electronic circuits, or microdevices—including microprocessors—that have been designed for use as electrical components, processors, computer memory, as well as countless special purpose uses in connection with consumer goods and industrial products; larger sized similarly-styled structures on the order of 1 cm and up, may also be referred to as 'chip'. The terms chip, integrated circuit (IC), and microchip are often used interchangeably within the electronics industry: the smaller microchips can hold a handful to tens-of-thousands of transistor/electrical devices (tiny chips of around $\frac{1}{16}$" square by $\frac{1}{30}$" thick); whereas larger-sized microchips sized on the order of $\frac{1}{2}$-inch$^2$, are capable of containing many millions of transistor/electrical devices.

V. Computer Memory and Computer Readable Storage

While the word 'memory' has historically referred to that which is stored temporarily, with storage traditionally used to refer to a semi-permanent or permanent holding place for digital data—such as that entered by a user for holding long term—more-recently, the definitions of these terms have blurred. A non-exhaustive listing of well known computer readable storage device technologies are categorized here for reference: (1) magetic tape technologies; (2) magnetic disk technologies include floppy disk/diskettes, fixed hard disks (often in desktops, laptops, workstations, etc.), (3) solid-state disk (SSD) technology including DRAM and 'flash memory'; and (4) optical disk technology, including magneto-optical disks, PD, CD-ROM, CD-R, CD-RW, DVD-ROM, DVD-R, DVD-RAM, WORM, OROM, holographic, solid state optical disk technology, and so on.

VI. Electromagnetic waves

It is well known that electric and magnetic fields are fundamentally fields of force that originate from electric charges. Whether a force field may be termed electric, magnetic, or electromagnetic (EM) hinges on the motional state of the electric charges relative to the point at which field observations are made. Electric charges at rest relative to an observation point give rise to an electrostatic (time-independent) field there. The relative motion of the charges provides an additional force field called magnetic. That added field is magnetostatic if the charges are moving at constant velocities relative to the observation point. Accelerated motions, on the other hand, produce both time-varying electric and magnetic fields, or electromagnetic fields. Exposure of a time-varying, typically sinusoidal magnetic field will induce an associated time-varying current ('alternating current' or AC) in a ferromagnetic sample such that it will emit EM energy. As further explained in connection with applicants' FIG. 1, this emission will typically be in the form of a cyclic transient response.

V. Quartz Crystal Microbalance (OCM)

A Quartz Crystal Microbalance is sometimes referred to as QMB ("Quartz MicroBalance") or EQCM ("Electrochemical Quartz Crystal Microbalance" when used by electrochemists). Physically, a QCM consists of a thin, usually round, slice of crystalline quartz with an electrode on each side. The electrode can be made of any metal, but gold is a common choice because it does not oxidize in air. If gold is used, a thin "undercoat" of chromium is usually put onto the quartz, first. If the two electrodes are put at different potentials an electric field results across the QCM, i.e. in the y-direction. Because of the piezoelectric properties of quartz, such an electric field in the y-direction couples to shear motion "around" the z-axis, and vice versa. The end result is that shear waves in the quartz, in which the mechanical displacement is in the x-direction (the "electric axis") are coupled to voltage between the electrodes. QCMs are traditionally used as sensitive detectors of mass deposited on them. This added mass decreases the resonant frequency of the QCM. By measuring the decrease in the resonant frequency of the QCM, and knowing something about the physics of the QCM, one can calculate the added mass per unit area on the QCM. QCMs can measure amounts of deposited material with an average thickness of less than a single atomic layer—hence the 'microbalance' part of their name.

Magnetoelastic sensors belong to the broad class of resonator sensors, as do piezoelectric acoustic wave sensors and quartz crystal microbalance (QCM) sensors. Tracking the resonant behavior of these types of sensors enables physical property measurements including pressure, temperature, liquid density and viscosity, and fluid flow velocity and direction, as explained above. Furthermore in combination with functional surfaces that change mass or elasticity in response to the analyte of interest the sensor platform can be used for biological or chemical sensing. Where a transient response is expected, practical applications require accurate and efficient measurement of the two information-bearing parameters: resonance frequency, signal amplitude, and damping. In earlier work—K. Zeng, K. G. Ong, C. Mungle, and C. A. Grimes, Rev. Sci. Instruments Vol. 73, 4375–4380 (December 2002)—one or more of the applicants reported a unique frequency counting technique that determines the resonance frequency of a sensor by counting, after termination of the excitation signal, the zero-crossings of the transitory ring-down oscillation. Damping was not addressed—so conventional techniques were employed.

The damping information associated with a transient response received by a sensor element has been conventionally extracted from the frequency spectrum by calculating the half-power point bandwidth, with spectrum analysis involving either steady-state response analysis using a lock-in amplifier or FFT analysis of the transient response. The use of either a lock-in amplifier or FFT analysis imposes a severe limitation to practical application of resonator-type sensor units in real-world operation. To address these issues, a new technique that adequately factored in damping of the transient response was needed. The technique and associated circuitry of the invention was developed for practical application employing a unique circuitry implementation, for extracting valuable information utilizing resonator-type sensing devices.

SUMMARY OF THE INVENTION

It is a primary object of this invention to provide a technique and associated circuitry for: (a) calculating a damping factor, e.g., a damping ratio represented by $\zeta$, or a quality factor Q which is related to a damping ratio, $\zeta \approx 1/2Q$, for a transient signal received, having been emitted from a resonator-type sensor element; (b) determining amplitude, A, of the transient signal; or (c) generating a frequency response dataset of interrelated points for the transient signal. In each characterization, a threshold comparison circuit is included for converting the transient signal received into a first and second digital waveform (of pulses, a square wave, etc.); the first digital waveform represents cycle crossings of the transient signal associated with a first threshold value, and the second digital waveform represents cycle crossings of the transient signal associated with a second threshold value. The transient signal may be converted, likewise, into third, fourth, and so on, digital waveforms, whereby the third digital waveform represents cycle crossings of the transient signal associated with a third threshold value, the fourth digital waveform represents cycle crossings of the transient signal associated with a fourth threshold value, and so on. Respective digital counters are included, each of which is adapted for determining a total number of cycles of the first, second, third, fourth, and so on, digital waveform. A processing unit of suitable speed and capacity is employed for calculating the damping factor, determining an initial amplitude for the transient response captured, and/or generating a frequency response dataset—according to the invention.

In a first characterization of the invention, the processing unit preferably calculates the damping factor using the first and second threshold values, and a difference between the second and first total cycles so counted, e.g., represented by $\Delta N = N_2 - N_1$. For example, the damping factor can be a damping ratio, $\zeta$, as expressed:

$$\zeta \approx \frac{\ln(A_1/A_2)}{2\pi(N_2 - N_1)};$$

wherein the first and second threshold values are represented, respectively, by $A_1$ and $A_2$. Or the damping factor could be expressed as a quality factor Q which is related to damping ratio, $\zeta \approx 1/2Q$, with damping ratio, $\zeta$, governed by the above expression.

The resonator-type sensor element may be of any suitable type excitable by way of an emission from a unit adapted for transmitting energy comprised of sinusoidal waves, pulse waves, square waves, triangular excitation waves, etc. Thus, the element is preferably a magnetoelastic element, a quartz crystal microbalance (QCM) element, piezoelectric acoustic wave element, and so on. The circuitry can include a receiver-element for receiving the transient signal in electrical communication with the threshold comparison circuit and a microcontroller unit comprising the first and second digital counters and the processing unit. Where the resonator-type sensor element is a magnetoelastic resonant element the receiver-element is preferably a solenoid coil. Other features can be included such as: (a) a coil drive circuit comprising an amplifier having a tunable gain in electrical communication with the coil, and a first switch disposed between the coil and the coil drive circuit for disconnecting the drive circuit during receipt of the transient signal; (b) a second switch disposed between a direct current (dc) bias source and the coil to turn-on the dc bias during receipt of the transient signal; and (c) an inductive element disposed between the direct current (dc) bias source the coil.

A suitable processing unit can be used to calculate a resonance frequency, f, for the resonator-type sensor element wherein: resonance frequency is governed by the expression $$f = \frac{N_0}{MT_{CLK}};$$

the variable $N_0$, represents the total cycles counted by another of the digital counters; and $T_{CLK}$ represents a period of a reference clock waveform input into one of the digital counters—which is also adapted to determine a number of reference clock cycles, M, associated with that input reference clock waveform. The circuitry can further include a coil for receiving the transient signal, and a microcontroller unit comprising at least the first and second digital counters and the processing unit; whereby the coil is in electrical communication with the microcontroller unit through the threshold comparison circuit.

In another aspect, the third digital counter (e.g., "Timer 0" identified in FIG. 7, associated with $N_0$) may be internal as part of the microcontroller unit, or external to and in electrical communication with the microcontroller unit. One of the digital counters (e.g., "Timer 1" or "Timer 2" in FIG. 7) may be given the capability of determining a number of reference clock cycles (e.g., $M_{CLK}$) associated with a reference clock waveform in addition to determining a total number of cycles of the first digital waveform. The third threshold value, e.g., such as that represented by $A_0$ (FIG. 7)

has a value greater than 0 Volts, and preferably a value greater than 2 nV, i.e., some value at least slightly larger than 0 V but, of course, less than the power supply voltage selected for the threshold comparison circuit. The threshold amplitude $A_0$ may be selected slightly above 0 V to reduce noise. Threshold voltage values are selected in connection with the resonator-type sensing elements employed, e.g., piezoelectric devices are operational for $A_0$ from 50 V to 200 V, or a voltage amplifier may be included with the circuitry so that operational threshold voltage, $A_0$, is selected from 10 V–12 V. The microcontroller unit may further be adapted for generating a frequency response dataset of total-cycle values counted as a function of frequency. This unique frequency response dataset may relate frequency as a function of one of the total cycles counted (e.g., $N_1$ or $N_2$ or $N_0$ as a function of frequency). Or, for closer approximation of frequency response for any given sensor element, the total-cycle value can be a sum of two or more total cycles counted (e.g., $N_1+N_2$,+and/or $N_N$).

In another characterization of the invention, circuitry for determining amplitude, A, of a transient signal received, having been emitted from a resonator-type sensor element, is described. The circuitry includes: (a) a threshold comparison circuit adapted for converting the transient signal received into a first and second digital waveform; the first digital waveform representing cycle crossings of the transient signal associated with a first threshold value, and the second digital waveform representing cycle crossings of the transient signal associated with a second threshold value; (b) a first and second digital counter, the first counter adapted for determining a first total cycles of said first digital waveform and the second counter adapted for determining a second total cycles of said second digital waveform; and (c) a processing unit for the determining of the amplitude. Where the first and second threshold values are represented, respectively, by $A_1$ and $A_2$, a respective value for total cycles is represented by $N_1$ or $N_2$, and a difference between the second and first cycles so counted, is represented by $\Delta N = N_2 - N_1$, the amplitude, A, may be determined by using either of the following expressions:

$$A = A_2 \left[\frac{A_1}{A_2}\right]^{N_2/\Delta N} ; \text{ or } A = A_1 \left[\frac{A_1}{A_2}\right]^{N_1/\Delta N}.$$

In yet another characterization, circuitry for generating a frequency response dataset for a transient signal received, having been emitted from a resonator-type sensor element, is disclosed. The circuitry comprises: (a) a threshold comparison circuit adapted for converting the transient signal received into a first and second digital waveform; the first digital waveform representing cycle crossings of the transient signal associated with a first threshold value (e.g., $A_1$), and the second digital waveform representing cycle crossings of the transient signal associated with a second threshold value (e.g., $A_2$); (b) a first and second digital counter, the first counter adapted for determining a first total cycles (e.g., $N_1$) of the first digital waveform and the second counter adapted for determining a second total cycles (e.g., $N_2$) of the second digital waveform; and (c) a processing unit for the generating of the frequency response dataset of total-cycle values counted as a function of frequency. As mentioned, this unique frequency response dataset may relate frequency as a function of one of the total cycles counted (e.g., $N_1$ or $N_2$ or $N_0$ as a function of frequency). Or, for closer approximation of frequency response for any given sensor element, the total-cycle value can be a sum of two or more total cycles counted (e.g., $N_1+N_2$,+and/or $N_N$).

As pointed out in connection with the other characterizations of the invention, the threshold comparison circuit can be further adapted for converting the transient signal received into a third digital waveform representing cycle crossings of the transient signal associated with a third threshold value (e.g., $A_0$). In this case, a third digital counter for determining a third total cycles (e.g., $N_0$) of the third digital waveform is employed. Also, a receiver-element (e.g., a solenoid coil) for receiving the transient signal is included in electrical communication with the threshold comparison circuit and a microcontroller unit. A microcontroller unit can be included for calculating a damping factor for the transient signal using the first and second threshold values, and a difference between the first and second total cycles so counted—as explained.

As one will appreciate, the many further distinguishing features set fourth above provide further unique capabilities to the core combination of features of the circuitry and associated method/technique for (a) calculating a damping factor, e.g., a damping ratio represented by $\zeta$, or a quality factor Q which is related to a damping ratio, $\zeta \approx 1/2Q$, for a transient signal received, having been emitted from a resonator-type sensor element; (b) determining amplitude, A, of the transient signal, and/or (c) generating a frequency response dataset of interrelated points for the transient signal—according to the invention.

Certain of the several unique features, and unique combinations of features, as supported and contemplated in the instant technical disclosure may provide one or more of a variety of advantages; among these are:

(a) Design flexibility/versatility—The basic structure of the circuitry and its functionalities are adaptable for use with resonator-type sensor elements from which transient signals are emitted in response to cyclical impulse, etc., excitation of a variety of possible shapes (sinusoidal waves, pulse waves, square waves, triangular excitation waves, etc.);

(b) The basic structure of the circuitry is adaptable for incorporation into a variety of packaging types tailored for use in a variety of environments, shaped and sized to accommodate space limitations;

(c) Multi-mode operability—The invention may function as multi-mode 'functionally agile' circuitry, providing an opportunity to obtain more than one parameter from the circuitry, as programmed. For example, resonance frequency may be obtained directly or by way of a frequency spectrum generated for the sensor element, and a damping factor is obtainable in the form of a damping ratio, quality factor, and so on, providing information as to transient shape of the signal(s) emitted from an excited sensor element, as received by a receiver; and (d) Manufacturability—The unique circuitry can be built using conventional or modified micro-components/devices employing known integrated circuit (IC) fabrication techniques for reproduction on a wide scale, allowing for assembly-line type production in an economically feasible manner.

These and other advantages will be appreciated by perusing the instant technical discussion, including the drawings, claims, and abstract, in light of drawbacks to, or limitations of, existing techniques identified (including results of applicants as reported earlier), or that may be uncovered.

BRIEF DESCRIPTION OF THE DRAWINGS

For purposes of illustrating the innovative nature plus the flexibility of design and versatility of the preferred circuitry and associated method/technique for (a) calculating a damping factor, e.g., a damping ratio represented by $\zeta$, or a quality factor Q which is related to a damping ratio for a transient signal received, having been emitted from a resonator-type sensor element; (b) determining amplitude, A, of the transient signal, and/or (c) generating a frequency response dataset of interrelated points for the transient signal—according to the invention and as disclosed hereby—the invention will be better appreciated by reviewing accompanying drawings (in which like numerals, if included, designate like parts). One will appreciate the many features that distinguish the instant invention from known techniques. The drawings have been included to communicate the features of the innovative circuit design and associated technique of the invention by way of example, only, and are in no way intended to unduly limit the disclosure hereof.

DETAILED DESCRIPTION OF EMBODIMENTS DEPICTED IN THE DRAWINGS

Reference will be made back-and-forth to FIGS. 1–21A,B so as to better appreciate the features of the new circuitry, its components/subcomponents, and associated method of the invention depicted throughout—as well as to incorporate examples of employing the unique circuitry and method of the invention, in sensing platforms. While examples provided herein showcase the use of magetoelastic sensor elements, other resonator-type sensor elements such as quartz crystal microbalance (QCM) elements, piezoelectric acoustic wave elements, etc. likewise are contemplated as they also emit transient responses from which useful information about an environment, analyte or sample of interest, may be gained.

Figure 1:
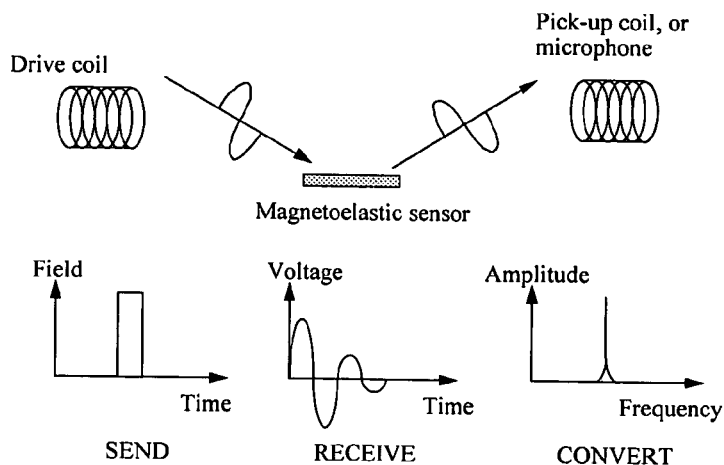
FIG. 1 schematically depicts an example of a preferred alternative resonator-type sensor element ("magnetoelastic sensor") excited by a magnetic field pulse ("send").

FIG. 1 schematically depicts an example of a preferred alternative resonator-type sensor element, labeled "magnetoelastic sensor," being excited by a magnetic field pulse ("send"). Upon excitation, the sensor resonates at a characteristic frequency ("receive"). The sensor vibrations result in the emission of a magnetic flux, which can be detected through use of a pick-up coil or microphone (depending on type/platform of sensor element). Magnetoelastic sensor elements are typically thick-film ribbons made of high permeability, magnetically soft amorphous ferromagnetic alloys—which are widely available (this material is also used as anti-theft magnetic markers). When excited with a magnetic-field pulse a magnetoelastic sensor element vibrates at its characteristic resonance frequency. The mechanical vibrations of the magnetostrictive sensor element in turn emit a magnetic flux allowing the sensor to be remotely detected with a receiving coil as illustrated. The low cost nature of the sensor platform makes practical the use of magnetoelastic sensors on a disposable basis.

A magnetoelastic sensor element vibrates at a fundamental resonance frequency that, independently of other environmental parameters, is inversely proportional to its length. The fundamental resonance frequency, f, of a ribbon-like sensor is governed by the expression, where L=length; E=modulus of elasticity; ρ=density:

$$f = \frac{1}{2L}\sqrt{\frac{E}{\rho}} \qquad \text{Eqn. (1)}$$

The resonance frequency of a magnetoelastic sensor element having a length of 4 cm to 6 mm (with an aspect ratio from 3 to 8) is typically from 60 kHz to 380 kHz, respectively.

A small mass load $\Delta m$ evenly deposited on a sensor of mass $m_0$ shifts the measured resonance frequency downward by an amount $\Delta f = f_{mass\ loaded} - f_r < 0$:

$$\Delta f = -f_r \frac{\Delta m}{2m_o} \qquad \text{Eqn. (2)}$$

Chemical or biological sensors can be fabricated by adhering a mass-changing (or elasticity changing) analyte responsive layer to the surface of the magnetoelastic sensor; as the mass of the layer changes so does the characteristic resonance frequency of the sensor. Tracking resonance frequency provides information as to a parameter of interest.

Practical application of a sensor technology is largely dependent upon the capabilities of the electronic measurement instrumentation that translates the transduction signal into a 'useful' signal, such as a microprocessor compatible voltage. Conventional instrumentation used in past for characterization of magnetoelastic sensors involved the use of relatively expensive, bulky general-purpose instruments, such as a lock-in amplifier, spectrum analyzer, signal generator, and oscilloscope. Use of such bulky expensive, general-purpose instruments imposes a significant limitation on many sensor applications.

Figure 2:
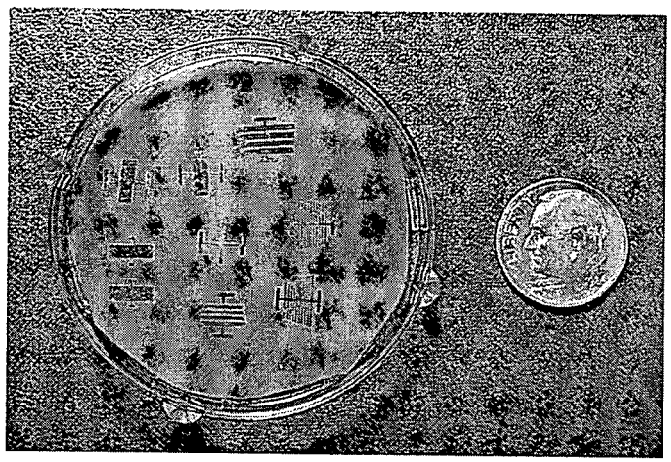
FIG. 2 is a top plan view of a cartridge containing several magnetoelastic sensor elements—an array of elements—fabricated by laser cutting ribbon-shaped magetoelastic material; a dime is also shown for scale comparison.
Figure 3:
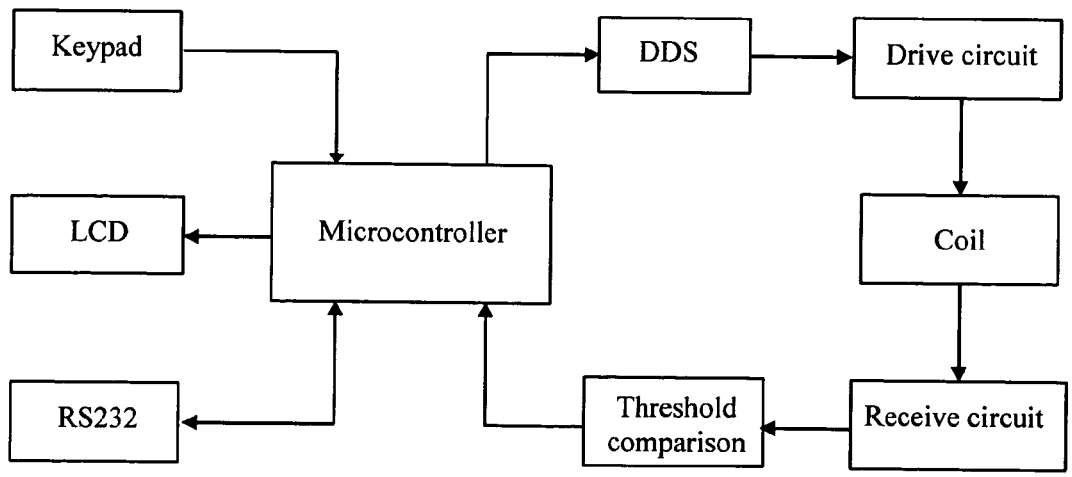
FIG. 3 is a block diagram of components of preferred circuitry of the invention; shown here is a microcontroller-based system.
Figure 4:
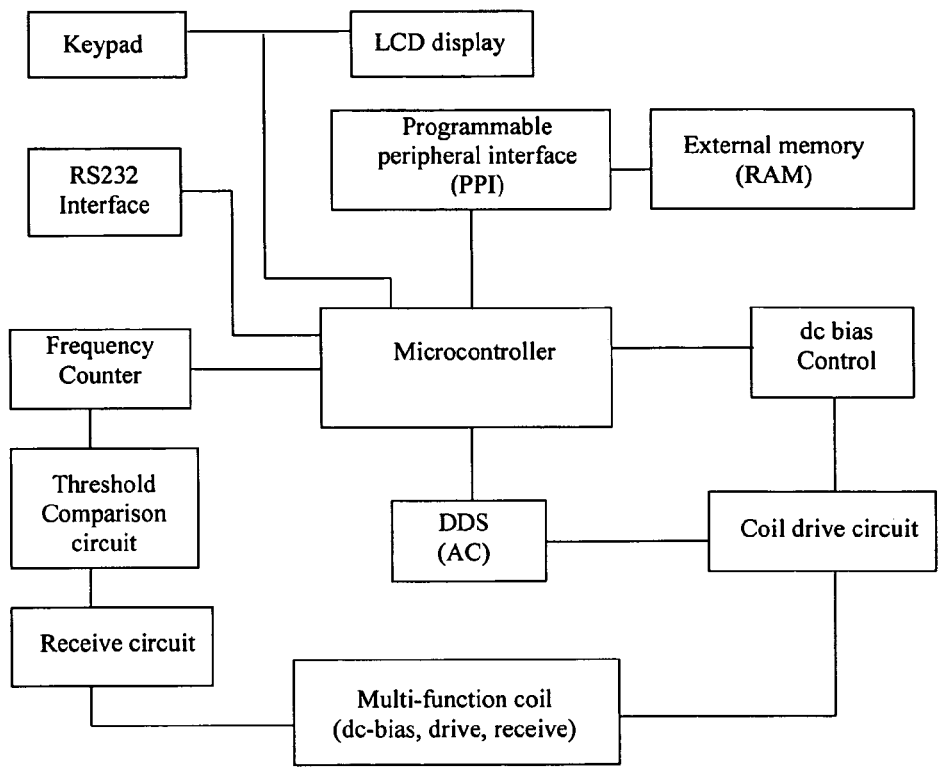
FIG. 4 is a block diagram of components of preferred circuitry of the invention; shown here is a microcontroller-based system—additional components identified.

FIG. 2 is a top plan view of a cartridge containing several magnetoelastic sensor elements—an array of elements—fabricated by laser cutting ribbon-shaped magetoelastic material; a dime is also shown for scale comparison. FIGS. 3 and 4 are block diagrams of components of preferred circuitry of the invention; shown here is a microcontroller-based system—additional components are identified, for reference, in FIG. 4. More detail is provided following a summary of rigorous engineering and mathematical analysis in support of the unique technique and method of the invention.

Magnetoelastic sensor elements, as well as the other resonator-type sensors, can be equivalently modeled as a mass-spring-friction system, described by a second-order differential equation:

$$m\frac{d^2y(t)}{dt^2} + c\frac{dy(t)}{dt} + ky(t) = f(t) \qquad \text{Eqn. (3)}$$

where m is the mass, k is the spring constant, c is the friction coefficient, y(t) is the displacement, and f(t) is the applied force. For convenience, one can rewrite the differential equation as $$\frac{d^2y(t)}{dt^2} + 2\zeta\omega_n\frac{dy(t)}{dt} + \omega_n^2 y(t) = \omega_n^2 x(t) \qquad \text{Eqn. (4)}$$

where $$\omega_n = \sqrt{\frac{k}{m}}$$

is the natural frequency, $$\zeta = \frac{c}{2m\omega_n}$$

is the viscous damping factor, and x(t)=f(t)/k is the external excitation that has the same unit as the response y(t). Letting X(s) and Y(s) be the Laplace transforms of x(t) and y(t), respectively, the result is $$Y(s) = \frac{\omega_n^2 X(s)}{s^2 + 2\zeta\omega_n s + \omega_n^2} + \frac{y'(0) + (s + 2\zeta\omega_n)y(0)}{s^2 + 2\zeta\omega_n s + \omega_n^2} \qquad \text{Eqn. (5)}$$

where y(0) is the initial displacement and y'(O) is the initial velocity. Eqn. (5) indicates that the system response Y(s) includes a steady-state response due to the applied excitation X(s) and a transient response due to the initial conditions y(0) and y'(0). The system is characterized by:

$$s^2 + 2\zeta\omega_n s + \omega_n^2 = 0 \qquad \text{Eqn. (6)}$$

and represented by the transfer function H(s) in S-domain, impulse response h(t) in time domain, and frequency response H(j ω) in frequency-domain. By definition, the transfer function is the ratio of the steady-state response and the applied excitation, thus $$H(s) = \frac{\omega_n^2}{s^2 + 2\zeta\omega_n s + \omega_n^2} \qquad \text{Eqn. (7)}$$

The transfer function H(s) and the impulse response h(t) form a Laplace transform pair. There are four cases of damping conditions: (a) Damping factor $\zeta=0$, un-damped, (b) $0<\zeta<1$, under-damped, (c) $\zeta=1$, critically damped, and (d) $\zeta>1$, over-damped. Typical damping factor values for magnetoelastic sensors range from 0.001 in air to 0.01 in viscous liquids.

The quality factor Q and damping factor ζ are related by:

$$Q = \frac{1}{2\zeta\sqrt{1-\zeta^2}} \qquad \text{Eqn. (8)}$$

Quality factor can also be calculated by:

$$Q = \frac{\omega_n}{\Delta\omega} \qquad \text{Eqn. (9)}$$

where $\Delta\omega$ is the half-power point bandwidth of the spectrum.

When the system is under-damped, the impulse response h(t) is an exponentially decaying oscillation, given by:

$$h(t) = \frac{\omega_n^2}{\omega_d}\exp(-\zeta\omega_n t)\sin(\omega_d t)u(t) \qquad \text{Eqn. (10)}$$

where u(t) is the unit step function indicating a causal system and $\omega_d\sqrt{1-\zeta^2}\omega_n$ is the frequency of the damped oscillation. From the second term on the right-hand side of Eqn. (5) one can obtain the transient response due to the initial conditions.

Figure 13:
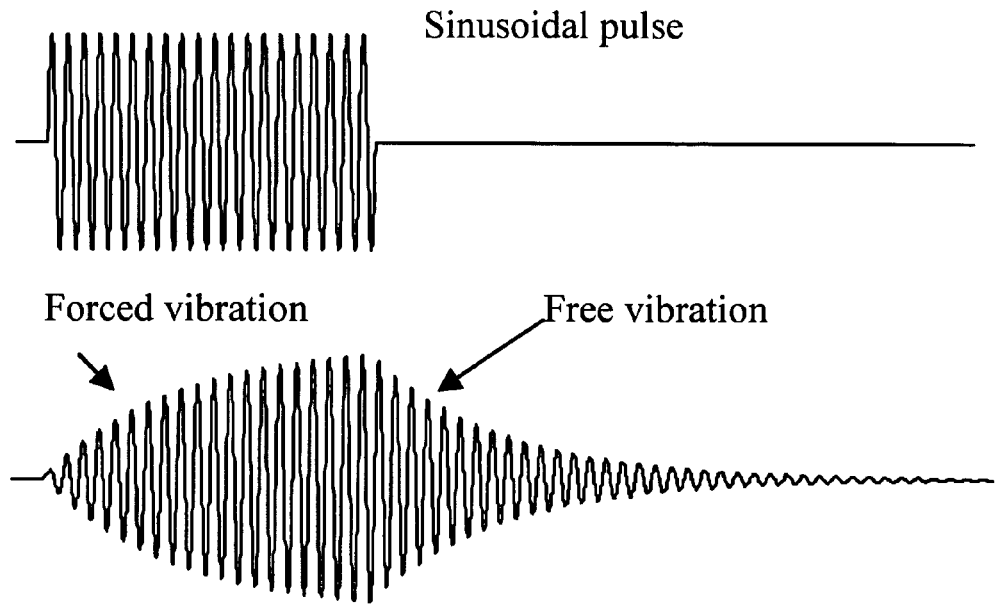
FIG. 13 depicts graphical representations of a model of the 'ring-and-listen' sensor interrogation technique, whereby the interrogation (drive) circuit excites the sensor element with an alternating magnetic field pulse (labeled "sinusoidal pulse").

Thus, consider the impulse response to be the transient response due to an initial velocity caused by the applied impulse. Sine wave pulse excitation has been used to excite the sensors into the resonant state since it tends to be more energy efficient than impulse excitation. FIG. 13 graphically represents a model using a Matlab™ simulation of the 'ring-and-listen' sensor interrogation technique, whereby, the interrogation (drive) circuit excites the sensor element with an alternating magnetic field pulse (labeled "sinusoidal pulse"), which in turn, results in the sensor mechanically vibrating (labeled "forced vibration") then once the interrogation pulse ends, becomes a form of "free vibration", as labeled). This is not unlike resultant 'ringing' of an acoustic church bell after being excited by the strike of a mallet. Both the simulation and actual measured response of a magnetoelastic sensor to a sine wave pulse, captured using a digital oscilloscope (not shown, here), confirm that the sensor's transient response has an exponentially decaying envelope, from which damping information is determined.

Figure 12:
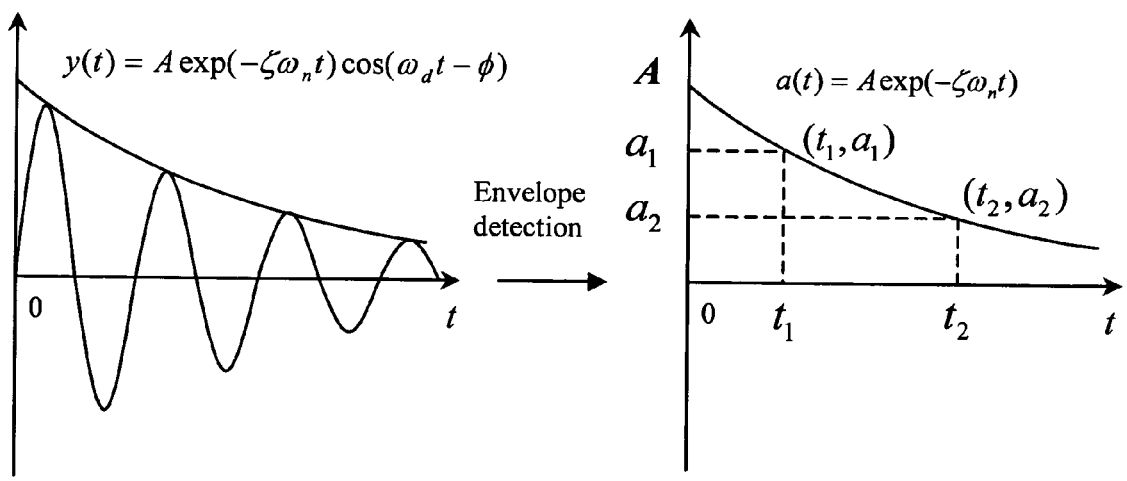
FIG. 12 depicts graphical representations of a model of the damping nature of a transient response, including mathematical expressions governing the response.

FIG. 12 graphically represents a model of the damping nature of a transient response, including mathematical expressions governing the response. From the amplitude envelope of an exponentially decaying signal, one may extract the damping ratio, since damping information is carried in the envelope of the oscillation. For an exponentially decaying oscillation signal:

$$y(t) = A\exp(-\zeta\omega_n t)\cos(\omega_d t - \phi) \qquad \text{Eqn. (11)}$$

$$a(t) = A\exp(-\zeta\omega_n t) \qquad \text{Eqn. (12)}$$

Let $\sigma = \zeta\omega_n$. Where the two points $(t_1, a_1)$, and $(t_2, a_2)$, are known, one can calculate $\sigma$ by the following manipulations:

$$a_1 = A\exp(-\sigma t_1) \qquad \text{Eqn. (13)}$$

$$a_2 = A\exp(-\sigma t_2) \qquad \text{Eqn. (14)}$$

$$a_1/a_2 = \exp(\sigma(t_2 - t_1)) \qquad \text{Eqn. (15)}$$

$$\sigma = \frac{\ln(a_1/a_2)}{t_2 - t_1} \qquad \text{Eqn. (16)}$$

Figure 14:
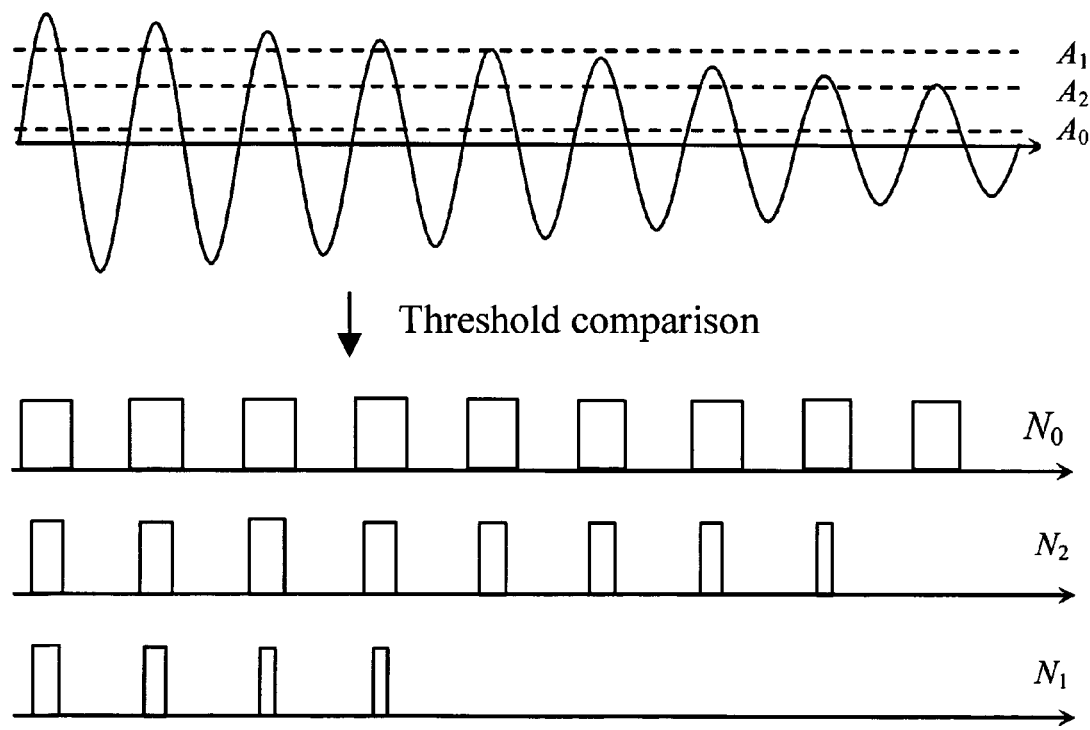
FIG. 14 depicts graphical representations of the threshold comparison operation: converting a transient response/signal into digital waveforms (here, for example, three waveforms are shown as digital pulse trains of a length/number of pulses $N_0$, $N_1$, $N_2$).

FIG. 14 depicts graphical representations of the threshold comparison operation: converting a transient response/signal into digital waveforms (here, for example, three waveforms are shown as digital pulse trains of a specific length/number of pulses labeled $N_0$, $N_1$, $N_2$). Each digital waveform results from the comparison of the transient signal with a respective amplitude threshold level (e.g., such as $A_0$, $A_1$, and $A_2$), according to the invention. Applying two thresholds, below labeled $a_1$ and $a_2$—interchangeably labeled throughout this discussion as $A_1$ and $A_2$—to the exponentially decaying oscillation, two series of digital pulses will result from threshold comparison. The number of pulses obtained by threshold $a_1$ is $N_1$, and the number of pulses obtained by $a_2$ is $N_2$. Next, the time(s) $t_1$ and $t_2$ can be calculated using the following approximations:

$$t_1 \approx N_1 T = N_1/f_d = 2\pi N_1/\omega_d \qquad \text{Eqn. (17)}$$

$$t_2 \approx N_2 T = N_2/f_d = 2\pi N_2/\omega_d \qquad \text{Eqn. (18)}$$

$$\Delta t = t_2 - t_1 \approx (N_2 - N_1)T = 2\pi(N_2 - N_1)/\omega_d \qquad \text{Eqn. (19)}$$

where T and $\omega_d$ are, respectively, the period and frequency of the exponentially decaying oscillation. Substituting Eqn. (19) into Eqn. (16) one obtains:

$$\sigma = \zeta\omega_n = \frac{\ln(a_1/a_2)}{\Delta t} = \frac{\ln(a_1/a_2)}{2\pi\Delta N/\omega_d} \qquad \text{Eqn. (20)}$$

Since $\omega_d = \sqrt{1-\zeta^2}\omega_n$, rewrite Equation (20) as $$\zeta\sqrt{1-\zeta^2} = \frac{\ln(a_1/a_2)}{2\pi\Delta N} \qquad \text{Eqn. (21)}$$

Uniquely it was then recognized that for small damping, a damping factor, e.g., damping ratio, ζ, or quality factor, Q, which is related thereto, $\zeta \approx 1/2Q$, can be determined by counting the crossings of two given thresholds (as labeled in FIG. 12):

$$\zeta \approx \frac{1}{2Q} = \frac{\ln(a_1/a_2)}{2\pi\Delta N} \qquad \text{Eqn. (22A)}$$

or, as interchangeably labeled using $A_1$ and $A_2$ with $\Delta N = N_2 - N_1$ (see FIG. 14), $$\zeta \approx \frac{\ln(A_1/A_2)}{2\pi(N_2 - N_1)}. \qquad \text{Eqn. (22B)}$$

Uniquely, making the substitutions of Eqn. (20) and Eqn. (21) into Eqn. (12) confirms that a value for an initial amplitude, A, of the oscillation can be obtained as follows:

$$A = a_2 \exp\left[\ln(a_1/a_2) \cdot \frac{N_2}{\Delta N}\right] = a_2 \left(\frac{a_1}{a_2}\right)^{N_2/\Delta N} \quad \text{Eqn. (23)}$$

or $$A = a_1 \exp\left[\ln(a_1/a_2) \cdot \frac{N_1}{\Delta N}\right] = a_1 \left(\frac{a_1}{a_2}\right)^{N_1/\Delta N} \quad \text{Eqn. (24)}$$

From the transient response of a resonator-type sensor, the oscillation frequency is determined by reciprocal frequency counting—the electronic implementation of which requires employing two of the timers (see FIGS. 7, 11, 14): one to count the received pulses and the other to act as a reference clock. The three timers ("Timer 0"–"Timer 2") of the microcontroller (e.g., as represented in FIGS. 3 and 4) can be programmed to run as either timers or counters. During frequency counting, Timer 0 is used as a counter to count the number of received digital pulses and Timer 1 or 2 may be used as a timer to count the number of reference clock pulses. The resonance frequency f can be calculated:

$$f = \frac{N_0}{MT_{CLK}} \quad \text{Eqn. (25A)}$$

where $N_0$ is the number of received digital pulses, M is the number of reference clock pulses, and $T_{CLK}$ is the reference clock period. To reduce noise threshold amplitude $A_0$ is chosen as a value slightly above zero. Measurement accuracy is directly related to the number of pulses for counting, with larger $N_0$ corresponding to higher accuracy. Since the sensor signal is transient and $N_0$ is limited, one can employ a repetitive interrogation (averaging) to improve measurement accuracy. Note that the resonance frequency value measured using this technique is the damped oscillation frequency rather than the natural frequency. For a second order damped oscillation system, the damped oscillation frequency $\omega_d$, the damping ratio, $\zeta$, and the natural frequency, $\omega_n$, are related by $\omega_d = \omega_n \sqrt{1-\zeta^2}$. Since the damping ratio of the magnetoelastic sensors is typically 0.001 to 0.01, $\omega_d$ is approximately the same as $\omega_n$ (within less than 0.005%).

As the applicants have reported (referenced above, K. Zeng, K. G. Ong, C. Mungle, and C. A. Grimes, Rev. Sci. Instruments Vol. 73, 4375–4380 (December 2002)), the frequency of an unknown periodic signal can be determined by counting the number of consecutive transits across a given threshold point, commonly chosen as zero, within a known period of time. For a periodic time-varying signal, frequency f is approximated by:

$$f = \frac{N}{\Delta t} = \frac{N}{MT_{CLK}} \quad \text{Eqn. (25B)}$$

where N is an integer representing the number of observed signal cycles, and $\Delta t$ is the total time interval that equals an integer M times the period of the reference clock $T_{CLK}$.

Frequency f can be determined by either counting N for a fixed time interval $\Delta t$ (classical frequency counting) or counting the number of clock ticks M for a fixed number of zero crossings N (reciprocal frequency counting). The frequency f by Eqn. (25B) is exact only when the time interval is an integer multiple of the detected signal period. For classical frequency counting with an arbitrary fixed time interval an error will be introduced when the actual number of cycles is a fraction between N and N+1; error is minimized with large N. However, reciprocal counting measures the number of clock ticks for a specified number of signal cycles, thus the error is within M and M+1 clock cycles. As long as the clock speed is higher than the frequency of the sensor M will be larger than N, which makes reciprocal counting a more accurate method. The absolute resolution for the reciprocal frequency counting technique can be expressed as:

$$\Delta f = \frac{N}{MT_{CLK}} - \frac{N}{(M+1)T_{CLK}} = \frac{N}{M(M+1)T_{CLK}} = f_{CLK} \frac{N}{M(M+1)} \quad \text{Eqn. (26)}$$

Turning once again to the block diagrams of FIGS. 3 and 4: A microcontroller-based system—including core and further distinguishing features—is depicted. Sensor instrumentation has components generally identified below as:

Sensor. The sensor is the transducer that converts the information about the about an environment, analyte or sample of interest, into a form, e.g., electrical signals, that can be used by the processing unit.

Sensor Interface. The mechanism for sensor interrogation. For example, in the magnetic detection of magnetoelastic sensors, solenoid coil(s) are used to drive the sensor and detect the sensor response.

Front-end Signal Conditioning. The sensor signal detected by the sensor interface needs to be conditioned for back-end signal processing. Signal conditioning normally involves filters and amplifiers.

Back-end Signal Processing. The information carried in the sensor signal is extracted through signal processing. Signal processing often involves the use of microprocessors.

Data Interpretation. The characteristic parameters of the sensor signal are, then, interpreted to provide parameters of interest, thus providing sensing information and data.

The operation of the sensing system (FIGS. 3 and 4) may be by way of a microcontroller unit when used as a stand-alone device, e.g., as a portable unit, though system control can be taken over by a computer via an RS232 interface during remote control operation mode. When used as a stand-alone device, a user may access the system through a keypad or other user interface and suitable display, e.g., an LCD display. The magnetoelastic sensor may be inserted inside a multi-functional coil excited by a coil driving circuit. The excitation signal may be composed of a dc biasing field generated by a dc bias control, and an ac drive field generated by a Direct Digital Synthesis (DDS) interface unit. The response of the sensor, as an analog signal, is fed through a receiving circuit, which includes a threshold comparison circuit and one or more external frequency counters (alternatively, the function of the frequency counter(s) can be performed by the high-speed microcontroller). A programmable peripheral interface may be included to expand the I/O ports of the microcontroller to accommodate additional components such as an external memory (for more data storage) in the system.

Figure 5:
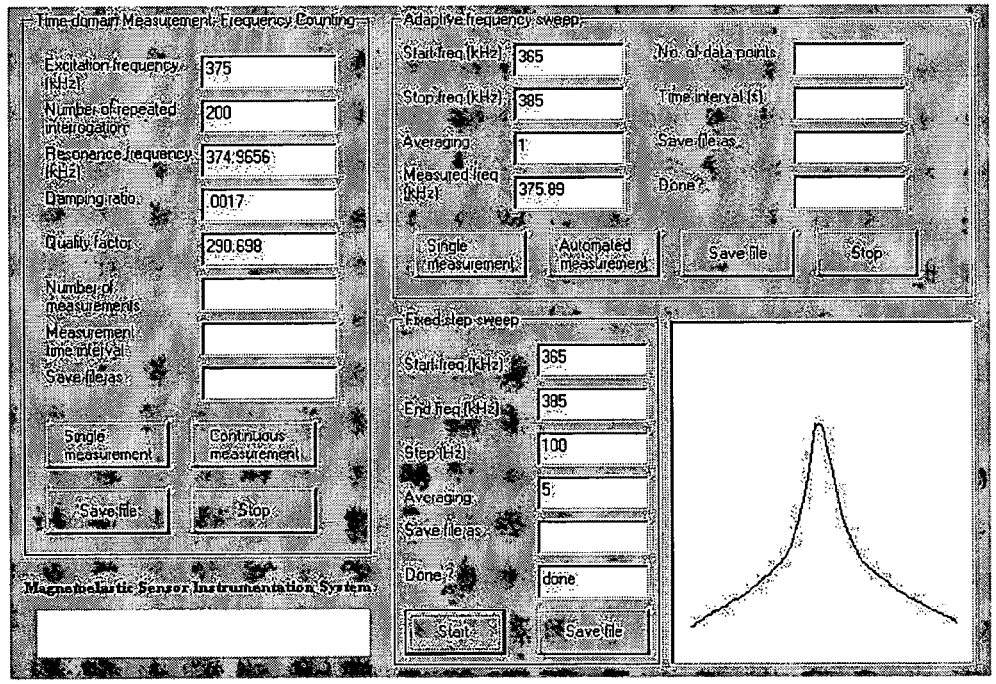
FIG. 5 is an embodiment of a graphic user interface (GUI) suitable for use in a sensing instrument/system into which the circuitry of the invention is incorporated.

FIG. 5 is an embodiment of a graphic user interface (GUI) suitable for use in a sensing instrument/system into which the circuitry of the invention is incorporated; depicted are various parameters of interest, and associated values, for reference only.

Figure 6:
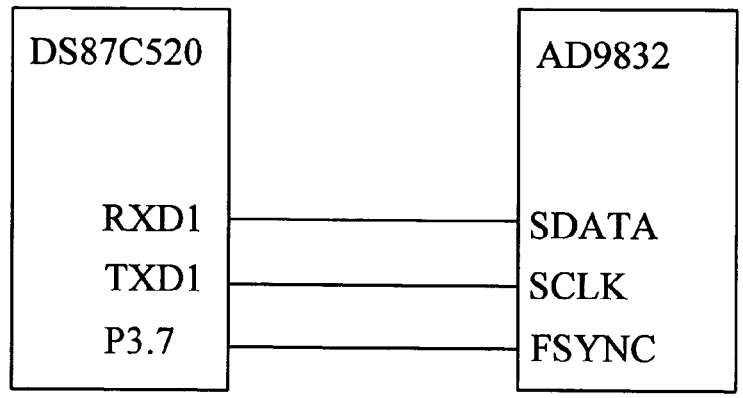
FIG. 6 is a block diagram of certain circuitry subcomponents, by way of example: Three-wire interface between conventional microcontroller unit, DS87C520, and a serial interface Direct Digital Synthesis (DDS) AD9832 chip manufactured by Analog Devices.

FIG. 6 is a block diagram of certain circuitry subcomponents, by way of example: Three-wire interface between conventional microcontroller unit, DS87C520, and a serial interface Direct Digital Synthesis (DDS) AD9832 chip manufactured by Analog Devices.

Figure 7:
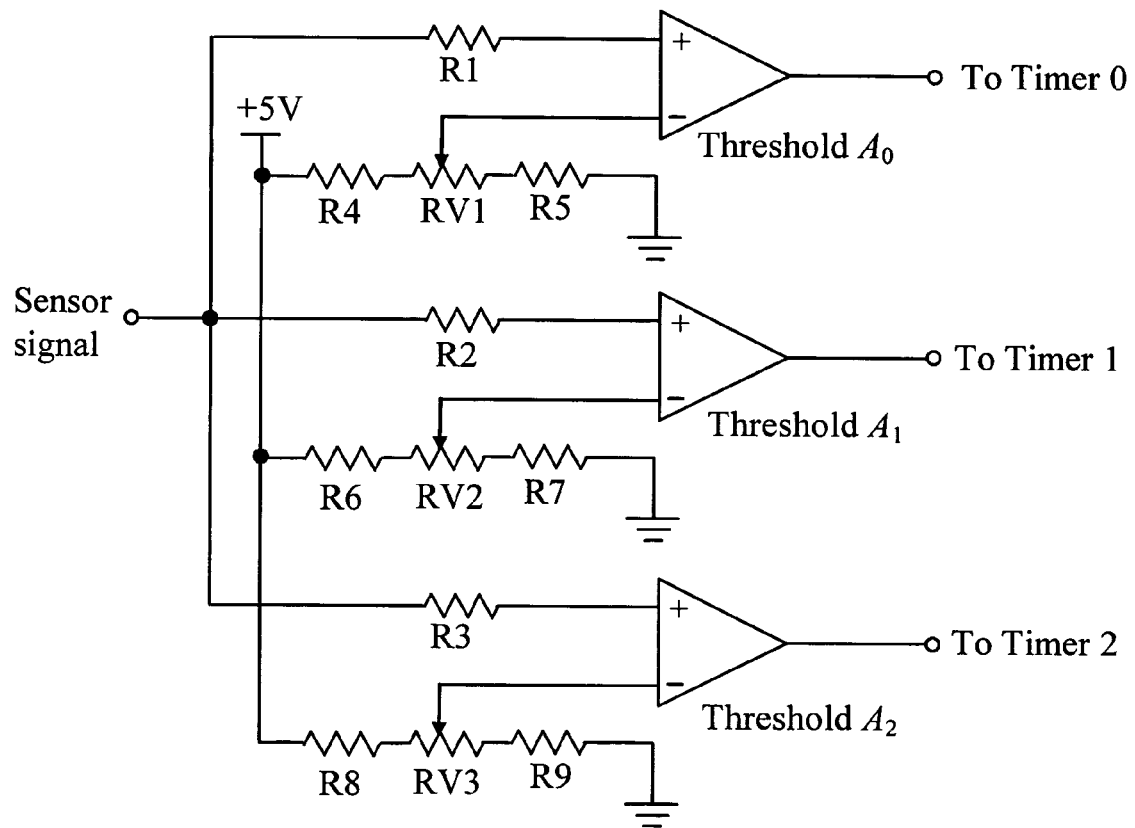
FIG. 7 is a circuit diagram of a threshold comparison circuit embodiment for converting an input transient signal ("senor signal") into digital waveforms—here, three.

FIG. 7 is a circuit diagram of a threshold comparison circuit embodiment for converting an input transient signal ("senor signal") into digital waveforms—here, three by way of example—respectively, output at Threshold $A_0$, Threshold $A_1$, Threshold $A_2$. The analog signal is fed into three digital comparators, as shown, with comparison threshold values tunable by respective potentiometers. The threshold comparison circuit generates three digital-pulse waveforms representing the threshold-crossings: at least one is used for frequency counting, and two used for damping-factor determination. The output of each respective comparator is fed into a timer/counter either internal to a microcontroller, or external and in electrical communication with the microcontroller. For example, during damping factor measurement two digital counters are used to count the number of crossings of the two different threshold amplitudes, with a damping factor (damping ratio or quality factor) then calculated using either Eqn. 22A/B.

Figure 8:
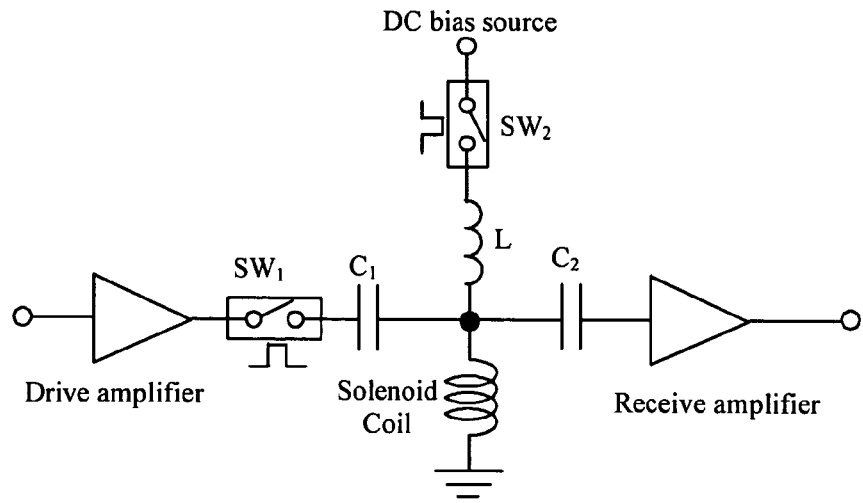
FIG. 8 is a circuit diagram of a multi-functional coil unit embodiment: The coil excites the sensor element; then after switching off the drive circuitry, the coil can receive the transient response emitted by the element.
Figure 9:
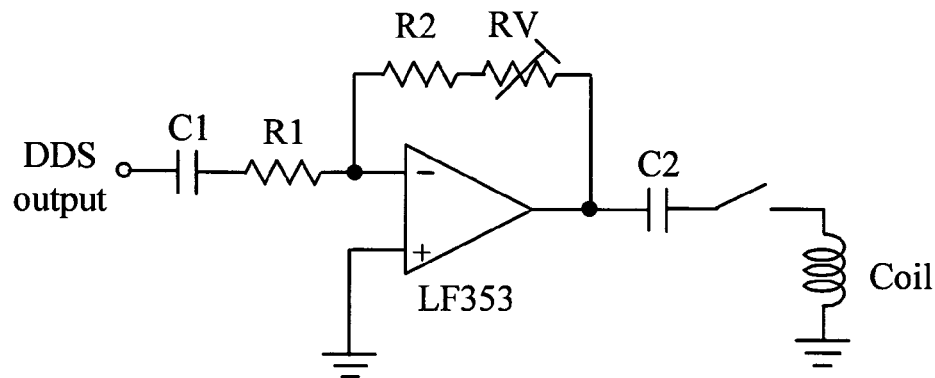
FIG. 9 is a circuit diagram of a drive subcomponent unit embodiment: The coil is driven by a drive circuit that, here, employs an op-amp with a tunable gain, for example.
Figure 10:
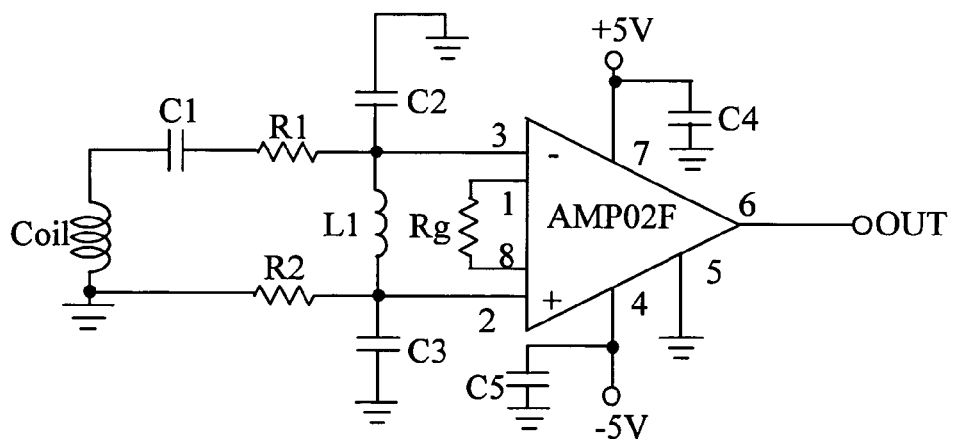
FIG. 10 is a circuit diagram of an amplifier unit embodiment: This unit is used to amplify the transient signal received by a sensor element, which might be very small.
Figure 11:
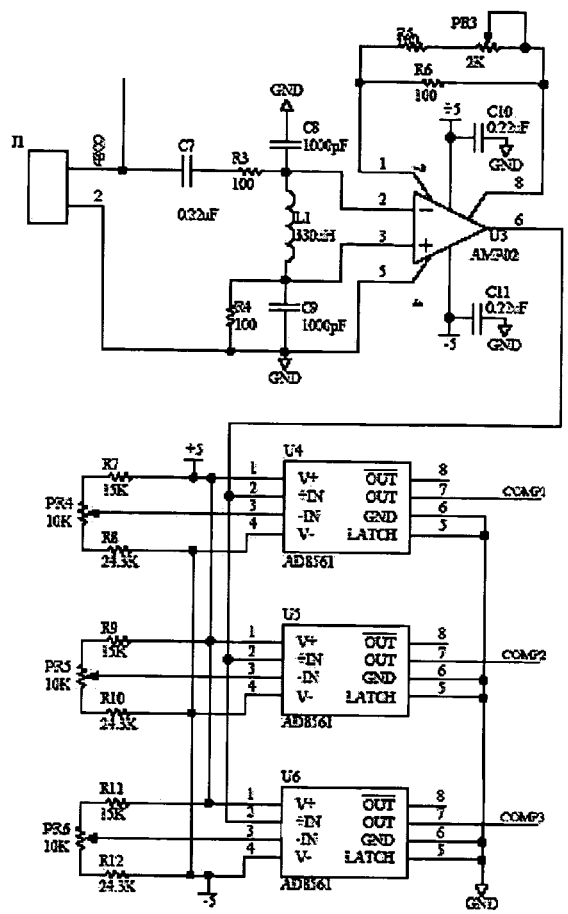
FIG. 11 is a circuit diagram of an embodiment whereby a threshold comparison circuit (FIG. 7) and an amplifier unit (FIG. 10) are interconnected for use according to the invention. Once again, component values are given by way of example only.

FIG. 8 is a circuit diagram of a multi-functional coil unit embodiment: The coil excites the sensor element; then after switching off the drive circuitry, the coil can receive the transient response emitted by the element; also, dc bias source can be connected. FIG. 9 is a circuit diagram of a drive subcomponent unit embodiment: The coil is driven by a drive circuit that, here, employs an op-amp with a tunable gain, for example. FIG. 10 is a circuit diagram of an amplifier unit embodiment: This unit is used to amplify the transient signal received by a sensor element, which might be very small (e.g., mV range) for certain sensor types/platforms. FIG. 11 is a circuit diagram of an embodiment whereby a threshold comparison circuit (FIG. 7) and an amplifier unit (FIG. 10) are interconnected for use according to the invention. Once again, component values are given by way of example only.

Figure 15:
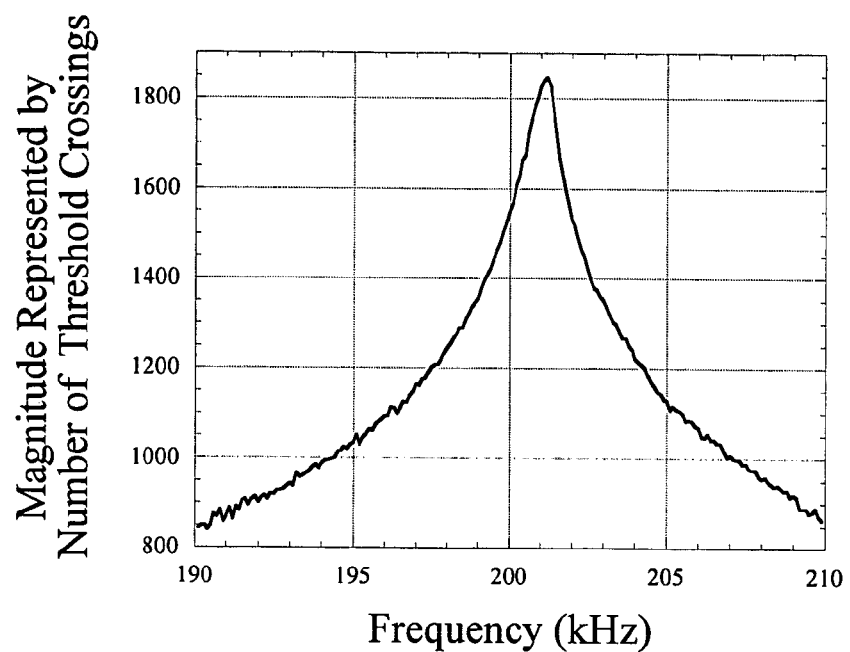
FIG. 15 is a graphical representation of a frequency response dataset for a transient signal received from an example magnetoelastic element; the peak is ~201 kHz.

FIG. 15 is a graphical representation of a frequency response dataset for a transient signal received from an example magnetoelastic element; the peak is ~201 kHz, representing the resonant frequency for this element embodiment. Signal magnitude is represented here along the y-axis, as the total-cycle values counted—it is plotted as a function of frequency along the x-axis. While one can use total cycles counted by any one of the three counters, a better approximation of the sensor's frequency spectrum is to plot a sum of two or more total cycles counted (e.g., $N_1+N_2$,+ and/or $N_0$). The plot in FIG. 15 is of a sum of all three total cycles counted (as labeled in FIG. 14, $N_1+N_2+N_0$) as a function of frequency. As one can appreciate, this is a close approximation of the frequency spectrum obtained for this sensor element as represented in FIG. 16.

Figure 16:
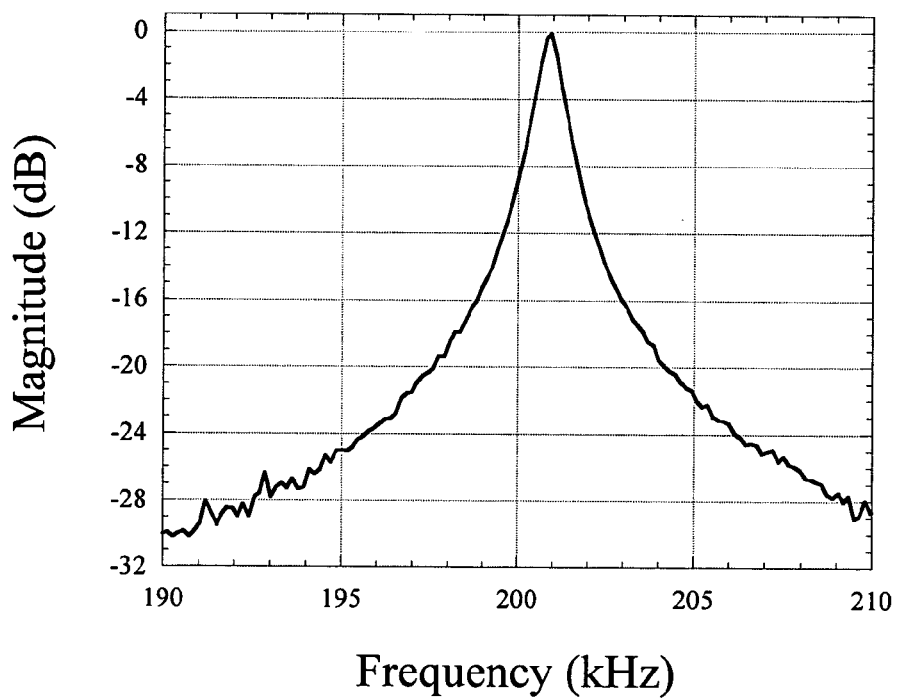
FIG. 16 is a graphical representation of a frequency spectrum for the example magnetoelastic sensor element of FIG. 15, obtained by performing a conventional FFT (Fast Fourier Transform) on the transient response captured using an oscilloscope.

FIG. 16 is a graphical representation of a frequency spectrum for the example magnetoelastic sensor element of FIG. 15, obtained by performing a conventional FFT (Fast Fourier Transform) on the transient response captured using an oscilloscope. A comparison of this plot and that in FIG. 15 shows each plot provides similar valuable information, confirming that the unique technique of the invention is a very close and useful approximation.

Figure 17:
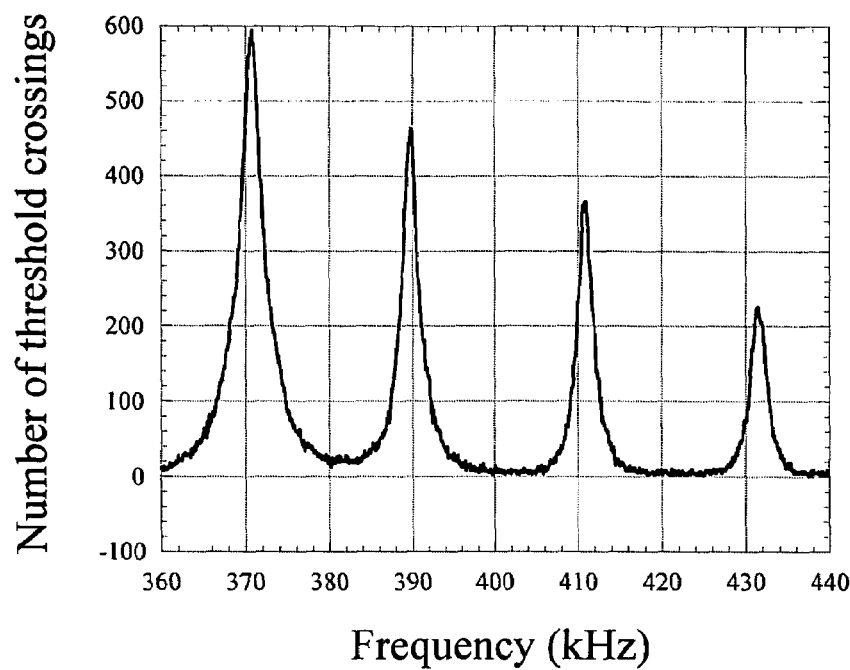
FIG. 17 depicts graphical representations of a frequency response dataset for each of four example magnetoelastic elements arranged in an array similar to that in FIG. 2.

FIG. 17 depicts graphical representations of a frequency response dataset for each of four example magnetoelastic elements arranged in an array similar to that depicted in FIG. 2. Signal magnitude is represented here along the y-axis, as the total-cycle values counted—it is plotted as a function of frequency along the x-axis. The sensor array for this example was cut from 28 micron thick magnetoelastic ribbon. The four sensors for which total cycle counts were made ranged in length from 6 mm, 5.5 mm, 4.5 mm, and 3.5 mm, each with a length-to-width aspect ratio of 14. Associated individual resonant frequencies of the four example elements, as shown (at peaks) are: 371 kHz, 390 kHz, 411 kHz, and 432 kHz. As one can appreciate, the magnitude of the sensor response decreases with increasing resonance frequency, which is expected since the higher frequency sensor elements are smaller in size, and generate less magnetic flux upon excitation according to the invention. In operation, a frequency sweep may be done for each sensor element of the array to obtain a frequency response plot as shown in FIG. 17, having four peaks, one for each element. From the frequency response plot, the resonance frequency of each individual sensor element is determined by finding the frequency of the corresponding peak. Parameters of interest such as amplitude, A, and damping of each sensor element may then be sequentially calculated/obtained.

Figure 18:
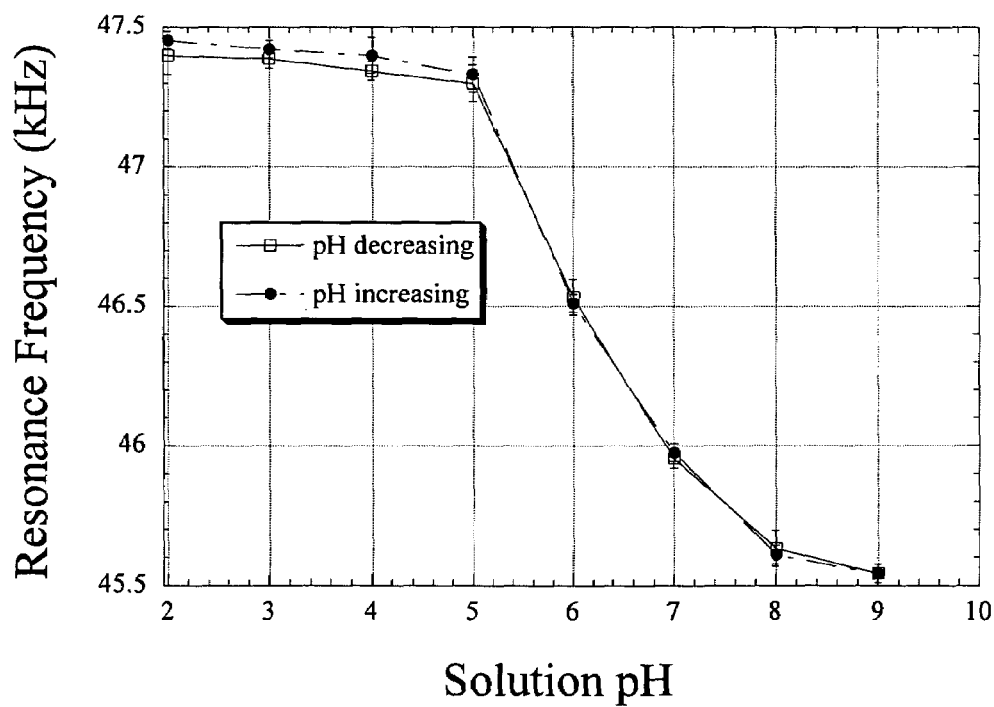
FIG. 18 depicts graphical representations of resonant frequency of an example magnetoelastic pH sensor—data obtained employing the unique digital waveform counting technique of the invention.

FIG. 18 depicts graphical representations of resonant frequency of an example magnetoelastic pH sensor—data obtained employing the unique digital waveform counting technique of the invention—depicting resonant frequency for an environment (e.g., a solution) while pH values are increased and while pH values are decreased, as labeled. When coupled with a reversible, mass-changing pH-responsive hydrogel, magnetoelastic sensors can be used as pH sensors. The pH dependent swelling or shrinking response of the polymer causes a mass change and hence a shift in the sensor resonance frequency; this can be monitored using the unique frequency counting technique and associated circuitry of the invention to measure and calculate parameters of interest. The resonance frequency decreases when the pH is switched from low to high, indicating that the polymer gel is swelling and hence increasing in mass. Conversely, the resonance frequency increases when the pH is switched from high to low indicating that the polymer gel is shrinking thus decreasing in mass. As shown in FIG. 18, for a pH change from 4.4 to 8.5 the average change in resonance frequency is 506 Hz/pH, corresponding to a change in sensor resonance frequency of approximately 1%/pH.

Figure 19:
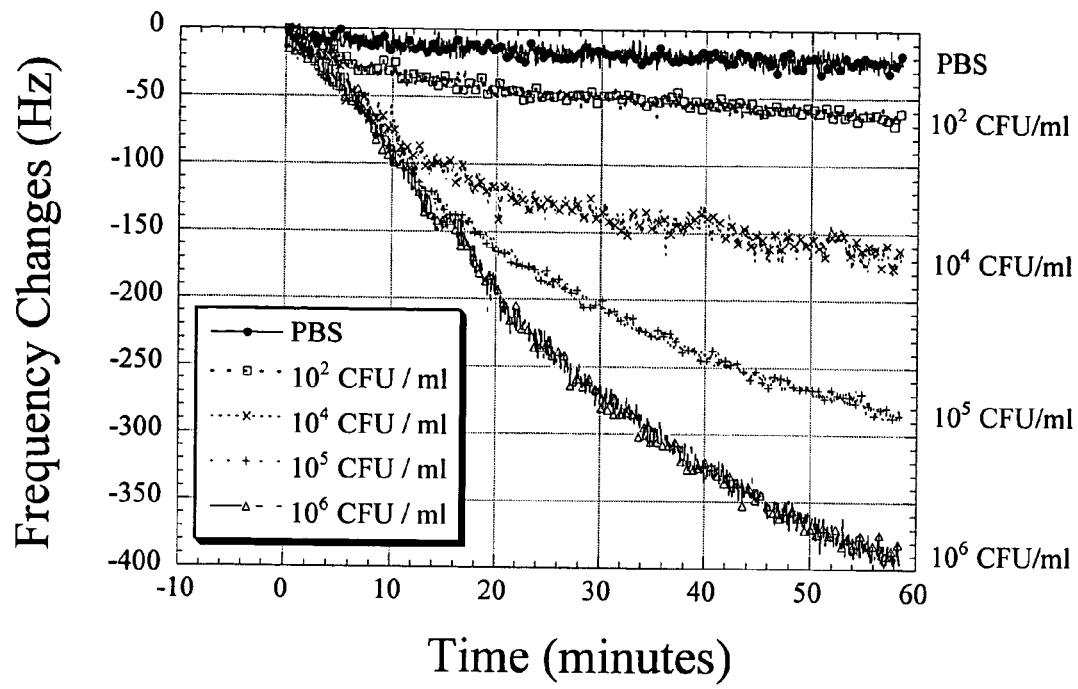
FIG. 19 depicts graphical representations of the frequency response of magnetoelastic sensors to *E. coli* O157:H7 concentrations ranging from $10^2$ to $10^6$ CFU/ml (in pH 10.0 PBS containing BCIP) as a function of sensor immersion time.

FIG. 19 depicts graphical representations of the frequency response of magnetoelastic *E. coli* O157:H7 sensors to *E. coli* O157:H7 concentrations ranging from $10^2$ to $10^6$ CFU/ml (i.e., concentrations of $10^2$ to $10^6$ cells/ml, in pH 10.0 PBS containing BCIP) as a function of sensor immersion time. This embodiment comprises a mass-sensitive magnetoelastic immunosensor for detection of *Escherichia coli* O157:H7, based on immobilization of affinity-purified antibodies attached to the surface of a magnetoelastic sensor. This sensor platform was used to monitor antibody-antigen reactions with an enzyme catalytic precipitation scheme that amplifies the resultant mass change. From data obtained according to the unique digital waveform counting technique of the invention (FIG. 19), one can appreciate that the rate of resonance frequency change and magnitude of resonance frequency change increase with increasing *E. coli* O157:H7 concentration. The background change in resonance frequency due to non-specific binding of the AP-labeled anti-*E. coli* antibody is approximately 20 Hz after 50 minutes; there is a 60 Hz change in resonance frequency for $10^2$ CFU/ml of *E. coli* O157:H7 over the same period.

Figure 20:
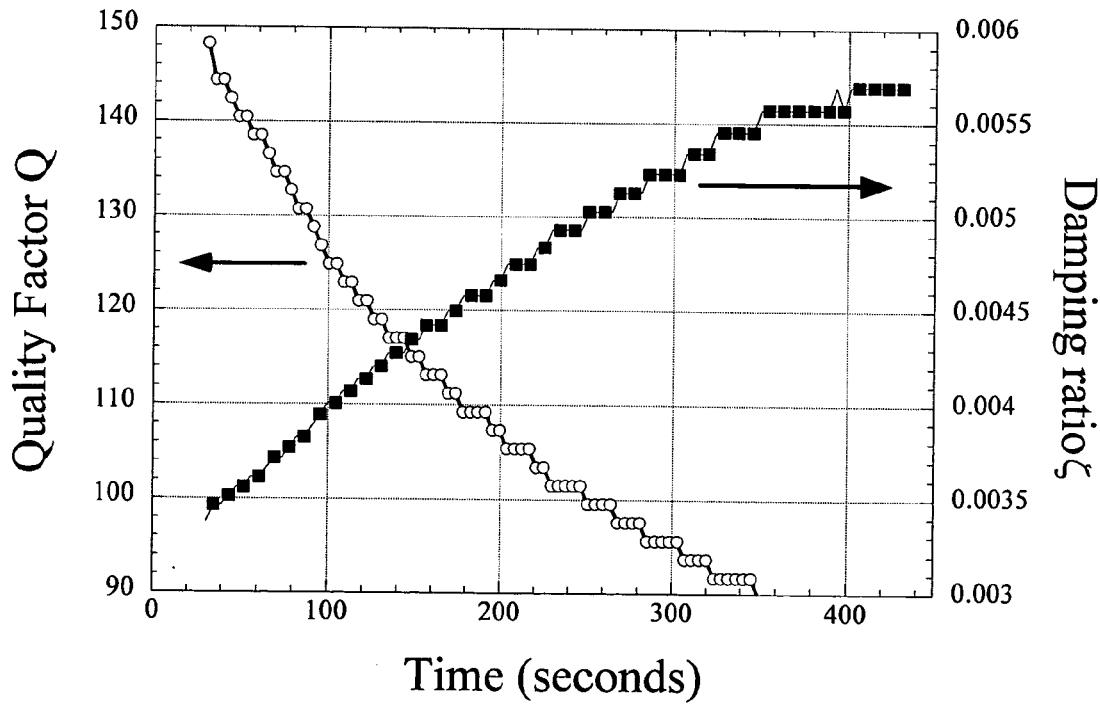
FIG. 20 depicts graphical representations of how damping ratio $\zeta$ and quality factor Q of an example magnetoelastic sensor onto which Elmer's® glue has been placed, changes over time (~7 minutes).

FIG. 20 depicts graphical representations of how damping ratio, ζ, and quality factor, Q, of an example magnetoelastic sensor onto which a drop of Elmer's® carpenter's wood glue has been placed (i.e., a thin film for which viscosity changes as it 'sets'), changes over time (~7 minutes)—resonance frequency of which was ~152 kHz. From data obtained according to the unique digital waveform counting technique of the invention, as can be appreciated, viscous damping force increases with glue drying (transforming/changing phases from liquid to solid), in parallel with a reduction in resonance quality factor, Q.

Figure 21A:
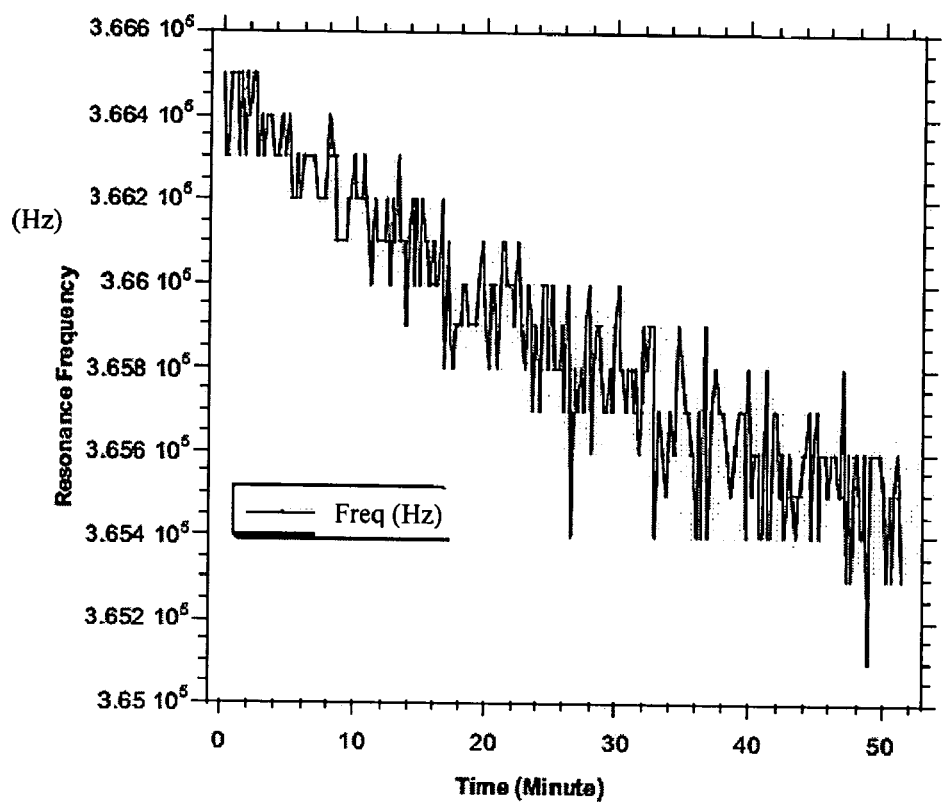
FIG. 21A is a graphical representation of changes in resonant frequency of an example magnetoelastic sensor onto which a mass has been placed, over time. Changes in frequency are quite noisy when tracked conventionally, as has been done for this plot.
Figure 21B:
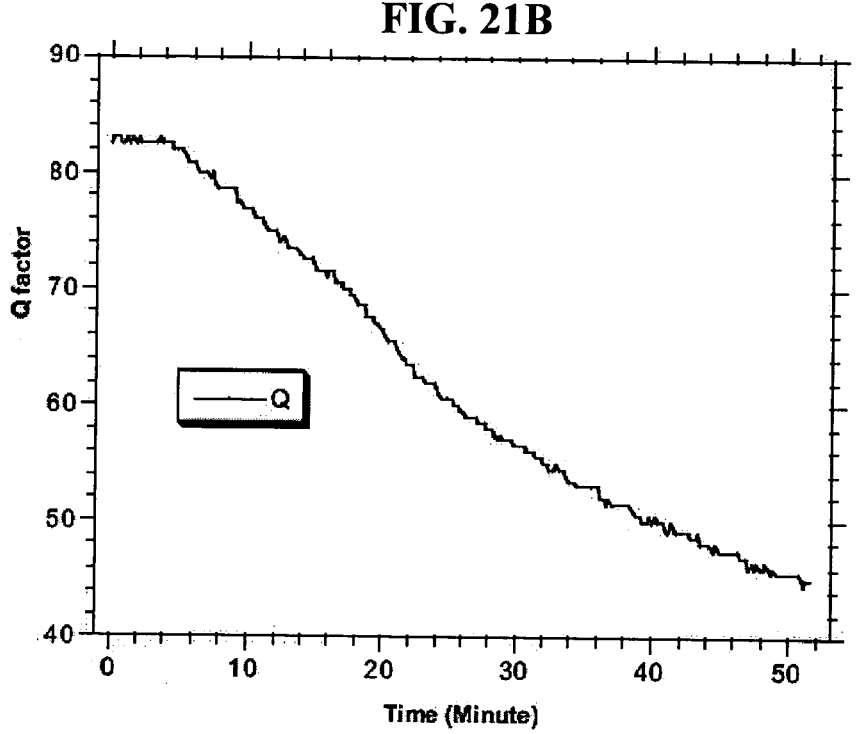
FIG. 21B is a graphical representation of changes in resonant frequency of an example magnetoelastic sensor onto which a mass has been placed, over time. In contrast to frequency data conventionally obtained (FIG. 21A), here, data was obtained according to the unique digital waveform counting technique of the invention ('cleaner' curve).

FIG. 21A is a graphical representation of changes in resonant frequency of an example magnetoelastic sensor onto which a mass has been placed, e.g., a protein toxin, over time. Changes in frequency are quite noisy when tracked conventionally, as has been done for this plot. FIG. 21B is a graphical representation of changes in resonant frequency of an example magnetoelastic sensor onto which a mass has been placed, e.g., a protein toxin, over time. In contrast to frequency data conventionally obtained as depicted in FIG. 21A, the data obtained according to the unique digital waveform counting technique of the invention as shown here (FIG. 21B), as can be appreciated, produces 'cleaner' curve.

EXAMPLES OF EMBODIMENTS OF THE INVENTION

By way of example only, two sensing systems are described, next. Example System 1 employs a high-speed DS87C520 microcontroller that can directly perform the frequency counting operation (no need for external counter units). Example System 2 uses a lower-cost AT89S53 microcontroller, an external counter(s) to precisely count the time for the frequency counting operation, and features software-controlled dc biasing field and thresholds. Along with a microcontroller (such as that depicted in FIGS. 3, 4), the following are employed: a threshold comparison circuit (e.g., FIGS. 7, 11) for signal conversion, an interrogation circuit that consists of a drive amplifier (e.g., FIG. 9), an instrumentation amplifier (e.g., FIG. 10), and a multifunctional interrogation coil (e.g., FIG. 8). The circuitry can be packaged into a compact plastic container, or other suitable material, along with a receiver-element such as a solenoid coil. For sensor interrogation, a 'ring-and-listen' technique is used to collect sensor information. A magnetic sinusoidal pulse is used to excite the sensor. The captured sensor response, i.e. sensor 'ring down,' is characterized using the novel threshold counting technique of the invention providing resonance frequency, damping factor, as well as the amplitude-frequency spectrum. A non-exhaustive list of uses for the circuitry/technique of the invention include: pH monitoring (e.g., FIG. 18), E. coli detection (e.g., FIG. 19), monitoring the drying of a layer (e.g., conventional carpenter's glue, FIG. 20), etc. The unique technique of the invention demands neither use of lock-in amplifier nor FFT, simplifying implementation in hardware and software. The user interface, such as that shown as GUI in FIG. 5, may be selected for handy adaptation for any of the specific sensing applications.

EXAMPLE 1

The microcontroller used in the design is a DS87C520 from Dallas Semiconductor Corporation. The DS87C520 microcontroller belongs to the 8051 family having the following characteristics: speed is up to 33 MHz crystal frequency, on-chip memory is 16 KB of ROM and 1 KB of MOVX RAM, has three internal 16-bit timers (labeled Timer 0–2) that are used in combination (FIGS. 7, 11, 14) to electronically implement the threshold-crossing counting technique for frequency measurement, damping measurement, and amplitude-frequency spectrum analysis according to the invention.

Direct digital synthesis (DDS) is a technique that is used to generate a frequency-agile, highly pure sine wave, or any arbitrary waveforms, from an accurate reference clock. The frequency of the output is digitally controlled by an N-bit digital word that allows sub-Hz frequency agility. The output waveform is normally reconstructed with a high-speed digital to analog converter (DAC). The magnetoelastic sensor system (e.g., FIG. 4) uses time-windowed periodic excitations. A DDS circuit is included to generate a sinusoidal wave-packet for sensor excitation, with the frequency digitally controlled by a 32-bit word. As shown in FIG. 6, a serial interface DDS chip AD9832 (manufactured by Analog Devices) which has a 32-bit frequency word was used. The DDS chip shares the same 20 MHz reference clock of the microcontroller, achieving a frequency resolution of 0.04 Hz. FIG. 6 depicts the three wire serial interface between AD9832 and the DS87C520 microcontroller. The Serial Port 1 in DS87C520 is programmed to operate in Mode 0 so that TXD1 provides serial clock and RXD1 sends the serial data into AD9832 through SDATA pin. The Data Synchronization Signal FSYNC is derived from the bit programmable P3.7. The AD9832 frequency control word is 32-bit, but the DS87C520 transmits data in 8-bit bytes. Therefore, the FSYNC signal is used to frame each control word into four write operations. Note that the microcontroller transmits the least significant bit (LSB) first, while the DDS chip accepts the most significant bit (MSB) first. Therefore, the serial data must be bit-reversed before transmission. The Serial Port 0 of the microcontroller is used for RS-232 interface, and Timer 2 is used to generate a baud rate of 9600 for the Mode 1 communication.

A threshold comparison circuit coverts the sensor signals into digital pulses. The outputs of the three comparators are fed to the three internal timers of the microcontroller. A solenoid coil of 2.5 cm in length and 1.6 cm in diameter was used for sensor excitation detection. A dc magnetic field is used to bias, or tune, the sensor element to an optimal operating point maximizing the amplitude of its output. If the sensors are not dc-biased with a suitable magnet during excitation, typically accomplished by adjacent placement of a magnetically hard thick film, a dc-bias field can be provided by the solenoid coil. As shown in the FIG. 8 embodiment, the coil serves three purposes: excitation, detection, and dc-biasing. Switch SW1 is turned on during sensor excitation, and off during sensor detection so that the detected sensor response will not feed through the drive circuitry. The dc-bias is controlled by switch SW2, with capacitors $C_1$ and $C_2$ used to block the dc-bias from the coil to the drive/receive circuitry. An inductor L is used to block the detected sensor response signal from the dc-bias circuit.

The amplitude of the excitation signal has an effect on sensor performance, depending upon the sensor element size, coil size, and the dc-bias field. Generally speaking smaller-sized sensing elements require a larger excitation force to overcome associated magnetic shape anisotropies and demagnetizing fields. If excitation voltage is too small, mechanical vibration of the sensor element is difficult—suffering from low signal-to-noise ratio(s). However when the excitation is too large, the elements may be overdriven into a nonlinear regime resulting in degraded sensor performance. For sensors of 200 kHz to 300 kHz, the optimal excitation voltage across a solenoid coil of 2.5 cm in length and 1.6 cm in diameter is ~200 mV corresponding to a magnetic field intensity of 30 A/m. The DDS has a fixed output of 2 volts peak-to-peak; a single stage op amp with a tunable gain is employed to adjust the excitation voltage, see FIG. 9.

Sensor reader circuitry was designed to process resonance frequency values from 50 kHz, corresponding to a sensor of 4.0 cm length, to 370 kHz corresponding to a 6 mm sensor. The magnetoelastic sensor element was placed inside the solenoid coil for taking sensor readings. Since the transient response received may be in the millivolt range, an amplifier is preferred. Shown by way of example in FIG. 10, is circuitry using an AMP02F manufactured by Analog Devices; this circuitry provides a voltage gain of 500 up to 450 kHz.

EXAMPLE 2

Core functionalities for the Example System 2 are the same as for Example System 1, plus the dc biasing field and the threshold voltages in the comparator circuit can be adjusted via software. This permits the system to monitor sensor elements of different sizes and shapes, where different biasing fields and thresholds are used, without requiring the change-out of circuitry components. Example System 2 uses a lower-cost microcontroller than that of Example System 1. The microcontroller unit AT89S53 distributed by Atmel of Example System 2 has similar features and performance, to that of the DS87C520, but the timer/counters speed is slower. If microcontroller speed is insufficient to perform certain of the counting/timing function(s), counter(s) that are external to the microcontroller are used. To perform a frequency counting operation, the timer/counters of the microcontroller have to track the number of cycles of the sensor transient signal, as well as the elapsed time during the counting operation. While the timer/counter in the AT89S53 is fast enough to count the number of cycles, its speed is not high enough to count the time. As a result, four 4-bit SN74F161A counters were used to perform a 16-bit counting operation to track the elapsed time during frequency counting. Since the input clock speed to the counters is 12 MHz, the external counters can measure time up to an accuracy of 83 ns. With a 16-bit counter, the system can measure a time period of up to 5.5 ms—enough for the sensor transient response. A four-output digital-to-analog converter (DAC) was used to control the three threshold voltages in the threshold comparison circuit (e.g., FIG. 7) and the dc biasing current. The DAC selected consisted of 4 output ports: VoutA, VoutB, VoutC, and VoutD. The first output VoutA was used to control the dc biasing current, and VoutB, VoutC, and VoutD were used for controlling the three threshold voltages in the comparison circuit.

While certain representative embodiments, examples, and details have been shown merely for the purpose of illustrating the technique and associated circuitry, including any microprocessor and/or microcontroller program code utilized to carry out functionalities according to the invention, those skilled in the art will readily appreciate that various modifications, whether specifically or expressly identified herein, may be made to any of the representative embodiments without departing from the novel teachings or scope of this technical disclosure. Accordingly, all such modifications are contemplated and intended to be included within the scope of the claims. Although the commonly employed preamble phrase "comprising the steps of" may be used herein in a method claim, applicants do not intend to invoke 35 U.S.C. §112 ¶6. Furthermore, in any claim that is filed herewith or hereafter, any means-plus-function clauses used, or later found to be present, are intended to cover at least all structure(s) described herein as performing the recited function and not only structural equivalents but also equivalent structures.

What is claimed is:

1. Circuitry for calculating a damping factor for a transient signal received having been emitted from a resonator-type sensor element, the circuitry comprising:
   (a) a threshold comparison circuit adapted or converting the transient signal received into a first and second digital waveform; said first digital waveform representing cycle crossings of the transient signal associated with a first threshold value, and said second digital waveform representing cycle crossings of the transient signal associated with a second threshold value, said first and second threshold value being less than or equal to an initial amplitude value of the transient signal received;
   (b) a first and second digital counter, said first counter adapted for determining a first total cycles of said first digital waveform and said second counter adapted for determining a second total cycles of said second digital waveform; and
   (c) a processing unit for the calculating of the damping factor using said first and second threshold values, and a difference between said second and first total cycles so counted.

2. The circuit of claim 1 wherein:
   (a) said damping factor is a damping ratio represented by $\zeta$, as expressed:

$$\zeta \approx \frac{\ln(A_1/A_2)}{2\pi(N_2 - N_1)}; \text{ and}$$

(b) said first and second threshold values being represented, respectively, by $A_1$ and $A_2$, said second and first total cycles represented, respectively, by $N_2$ and $N_1$, and said difference being represented by $\Delta N = N_2 - N_1$.

3. The circuitry of claim 1 wherein:
   (a) said damping factor is a quality factor Q which is related to a damping ratio, $\zeta \approx 1/2Q$, said damping ratio, $\zeta$, at being governed by the expression:

$$\zeta \approx \frac{\ln(A_1/A_2)}{2\pi(N_2 - N_1)}; \text{ and}$$

(b) said first and second threshold values being represented, respectively, by $A_1$ and $A_2$, said second and first total cycles represented, respectively, by $N_2$ and $N_1$, and said difference being represented by $\Delta N = N_2 - N_1$.

4. The circuitry of claim 1:
   (a) further comprising a receiver-element for location in proximity to the resonator-type sensor element for receiving the transient signal in electrical communication with said threshold comparison circuit and a microcontroller unit comprising said first and second digital counters and said processing unit; and
   (b) wherein the resonator-type sensor element is selected from the group of sensor elements consisting of magnetoelastic elements, quartz crystal microbalance (QCM) elements, and piezoelectric acoustic wave elements.

5. The circuitry of claim 4 wherein the resonator-type sensor element is a magnetoelastic element and said receiver-element is a coil nearby which said magnetoelastic element is located for said receiving of the transient signal emitted therefrom; and further comprising:
(a) a coil drive circuit comprising an amplifier having a tunable gain in electrical communication with said coil and a first switch disposed between said coil and said coil drive circuit for disconnecting said drive circuit during receipt of the transient signal;
(b) a second switch disposed between a direct current (dc) bias source and said coil to turn-on said dc bias during receipt of the transient signal; and
(c) an inductive element disposed between said direct current (dc) bias source and said coil.

6. The circuitry of claim 1:
(a) wherein said threshold comparison circuit is further adapted for converting the transient signal received into a third digital waveform representing cycle crossings of the transient signal associated with a third threshold value; and
(b) further comprising a third digital counter for determining a third total cycles of said third digital waveform.

7. The circuitry of claim 6 wherein:
(a) said first digital counter is further adapted to determine a number of reference clock cycles, M, associated with a reference clock waveform; and
(b) said processing unit is further adapted for calculating a resonance frequency, f, for the resonator-type sensor element said resonance frequency being governed by the expression $$f = \frac{N_0}{MT_{CLK}};$$

where said third total cycles is represented by $N_0$, and $T_{CLK}$ represents a period of said reference clock waveform.

8. The circuitry of claim 6:
(a) further comprising a coil for receiving the transient signal, and a microcontroller unit comprising said first and second digital counters and said processing unit; said coil in electrical communication with said microcontroller unit through said threshold comparison circuit; and
(b) wherein:
said third digital counter is external to, and in electrical communication with, said microcontroller unit;
said first digital counter is further adapted to determine a number of reference clock cycles associated with a reference clock waveform and
said third threshold value, represented by $A_0$, is a value greater than 2 nV.

9. The circuitry of claim 6:
(a) wherein the resonator-type sensor element is selected from the group of sensor elements consisting of magnetoelastic elements, quartz crystal microbalance (QCM) elements, and piezoelectric acoustic wave elements; and
(b) further comprising:
a coil for receiving the transient signal in electrical communication with said threshold comparison circuit and a microcontroller unit comprising said first, second, and third digital counters and said processing unit; and
said microcontroller unit further adapted for generating a frequency response data set of total-cycle values counted as a function of frequency, each said total-cycle value comprising one of said first, second, and third total cycles.

10. The circuitry of claim 9 wherein each said total-cycle value is a sum of at least said first and second total cycles counted.

11. The circuitry of claim 9 wherein each said total-cycle value is a sum of at least said first, second, and third total cycles counted.

12. A method for calculating a damping factor for a transient signal received, having been emitted from a resonator-type sensor element, the method comprising the steps of:
(a) converting the transient signal received into a first and second digital waveform; said first digital waveform representing cycle crossings of the transient signal associated with a first threshold value, and said second digital waveform representing cycle crossings of the transient signal associated with a second threshold value, said first and second threshold value being less than or equal to an initial amplitude value of the transient signal received;
(b) determining a first total cycles of said first digital waveform and determining a second total cycles of said second digital waveform; and
(c) calculating the damping factor using said first and second threshold values, and a difference between said second and first total cycles so counted.

13. The method of claim 12 wherein:
(a) said damping factor is a damping ratio represented by $\zeta$, as expressed:

$$\zeta \approx \frac{\ln(A_1/A_2)}{2\pi(N_2 - N_1)}; \text{ and}$$

(b) said first and second threshold values being represented, respectively, by $A_1$ and $A_2$, said second and first total cycles represented, respectively, by $N_2$ and $N_1$, and said difference being represented by $\Delta N = N_2 - N_1$.

14. The method of claim 12 wherein:
(a) said damping factor is a quality factor Q which is related to a damping ratio, $\zeta \approx 1/2Q$, said damping ratio, $\zeta$, being governed by the expression:

$$\zeta \approx \frac{\ln(A_1/A_2)}{2\pi(N_2 - N_1)}; \text{ and}$$

(b) said first and second threshold values being represented, respectively, by $A_1$ and $A_2$, said second and first total cycles represented, respectively, by and $N_2$ and $N_1$, and said difference being represented by $\Delta N = N_2 - N_1$.

15. The method of claim 12 further comprising the steps of:
(a) converting the transient signal received into a third digital waveform representing cycle crossings of the transient signal associated with a third threshold value; and (b) determining a third total cycles of said third digital waveform.

16. The method of claim 15 further comprising the steps of:
(a) determining a number of reference clock cycles, M, associated with a reference clock waveform; and
(b) calculating a resonance frequency, f, for the resonator-type sensor element, said resonance frequency being governed by the expression $$f = \frac{N_0}{MT_{CLK}};$$

where said third total cycles is represented by $N_0$, and $T_{CLK}$ represents a period of said reference clock waveform.

17. The method of claim 15 further comprising the step of generating a frequency response dataset of total-cycle values counted as a function of frequency each said total-cycle value comprising one of said first, second, and third total cycles.

18. The circuitry of claim 17 wherein each said total-cycle value is a sum of at least said first and second total cycles counted.

19. The circuitry of claim 17 wherein each said total-cycle value is a sum of at least said first, second, and third total cycles counted.

20. Circuitry for determining amplitude, A, of a transient signal received, having been emitted from a resonator-type sensor element, the circuitry comprising:
(a) a threshold comparison circuit adapted for converting the transient signal received into a first and second digital waveform; said first digital waveform representing cycle crossings of the transient signal associated with a first threshold value, and said second digital waveform representing cycle crossings of the transient signal associated with a second threshold value, said first and second threshold value being less than or equal to an initial amplitude value of the transient signal received;
(b) a first and second digital counter, said first counter adapted for determining a first total cycles of said first digital waveform and said second counter adapted for determining a second total cycles of said second digital waveform; and
(c) a processing unit for the determining of the amplitude by using:
said first and second threshold values represented respectively, by $A_1$ and $A_2$;
a value for at least one or said total cycles; and
a difference between said second and first total cycles so counted, said difference represented by $\Delta N = N_2 - N_1$, wherein said second and first total cycles are represented, respectively, by $N_2$ and $N_1$.

21. The circuitry of claim 20:
(a) further comprising a receiver-element for receiving the transient signal in electrical communication with said threshold comparison circuit and a microcontroller unit comprising said first and second digital counters and said processing unit;
(b) wherein the resonator-type sensor element is selected from the group of sensor elements, consisting of magnetoelastic elements, quartz crystal microbalance (QCM) elements, and piezoelectric acoustic wave elements; and
(c) wherein said amplitude, A, is governed by the expression:

$$A = A_2 \left[\frac{A_1}{A_2}\right]^{N_2/\Delta N}.$$

22. The circuitry of claim 20:
(a) further comprising a receiver-element for receiving the transient signal in electrical communication with said threshold comparison circuit and a microcontroller unit comprising said first and second digital counters and said processing unit;
(b) wherein the resonator-type sensor element is selected from the group of sensor elements consisting of magnetoelastic elements, quartz crystal microbalance (QCM) elements, and piezoelectric acoustic wave elements; and
(e) wherein said amplitude, A, is governed by the expression:

$$A = A_1 \left[\frac{A_1}{A_2}\right]^{N_1/\Delta N}.$$

23. A method for determining amplitude, A, of a transient signal received, having been emitted from a resonator-type sensor element, the method comprising the steps of:
(a) converting the transient signal received into a first and second digital waveform; said first digital waveform representing cycle crossings of the transient signal associated with a first threshold value, and said second digital waveform representing cycle crossings of the transient signal association with a second threshold value, said first and second threshold value being less than or equal to an initial amplitude value of the transient signal received;
(b) determining a first total cycles of said first digital waveform and determining a second total cycles of said second digital waveform; and
(c) determining the amplitude by using:
said first and second threshold values represented, respectively, by $A_1$ and $A_2$;
a value for at least one of said total cycles; and
a difference between said second and first total cycles so counted, said difference represented by $\Delta N = N_2 - N_1$, wherein said second and first total cycles are represented, respectively, by $N_2$ and $N_1$.

24. Circuitry for generating a frequency response dataset for a transient signal received, having been emitted from a resonator-type sensor element, the circuitry comprising:
(a) a threshold comparison circuit adapted for converting the transient signal received into a first and second digital waveform; said first digital waveform representing cycle crossings of the transient signal associated with a first threshold value, and said second digital waveform representing cycle crossings of the transient signal associated with a second threshold value, said first and second threshold value being less than or equal to an initial amplitude value of the transient signal received;
(b) a first and second digital counter, said first counter adapted for determining a first total cycles of said first digital waveform and said second counter adapted for determining a second total cycles of said second digital waveform;
(c) a processing unit for the generating of the frequency response dataset of total-cycle values counted as a function of frequency, each said total-cycle value comprising one of said first and second total cycles; and (d) wherein the resonator-type sensor element is selected from the group of sensor elements consisting of magnetoelastic elements, quartz crystal microbalance (QCM) elements, and piezoelectric acoustic wave elements.

25. The circuitry of claim 24 wherein each said total-cycle value is a sum of at least said first and second total cycles counted.

26. The circuitry of claim 24:
(a) wherein said threshold comparison circuit is further adapted for converting the transient signal received into a third digital waveform representing cycle crossings of the transient signal associated with a third threshold value; and
(b) further comprising a third digital counter for determining a third total cycles of said third digital waveform, wherein each said total-cycle value is a sum of at least said first, second, and third total cycles counted.

27. The circuitry of claim 26:
(a) further comprising a receiver-element for receiving the transient signal in electrical communication with said threshold comparison circuit and a microcontroller unit comprising said first, second, and third digital counters and said processing unit; and
(b) wherein said microcontroller unit is further adapted for calculating, a damping factor for the transient signal using said first and second threshold value, and a difference between said second and first total cycles so counted.

28. The circuitry of claim 27 wherein:
(a) said damping factor is a damping ratio represented by $\zeta$, as expressed:

$$\zeta \approx \frac{\ln(A_1/A_2)}{2\pi(N_2 - N_1)}; \text{ and}$$

(b) said first and second threshold values being represented, respectively, by $A_1$ and $A_2$, said second and first total cycles represented, respectively, by $N_2$ and $N_1$, and said difference being represented by $\Delta N = N_2 - N_1$.

29. The circuitry of claim 27 wherein:
(a) said damping factor is a quality factor Q which is related to a damping ratio, $\zeta \approx 1/2Q$, said damping ratio, $\zeta$, being governed by the expression:

$$\zeta \approx \frac{\ln(A_1/A_2)}{2\pi(N_2 - N_1)}; \text{ and}$$

(b) said first and second threshold values being, represented, respectively, by $A_1$ and $A_2$, said second and first total cycles represented, respectively, by $N_2$ and $N_1$, and said difference being represented by $\Delta N = N_2 - N_1$.

30. A method for generating a frequency response dataset for a transient signal received, having been emitted from a resonator-type sensor element, the method comprising the steps of:
(a) converting the transient signal received into a first and second digital waveform; said first digital waveform representing cycle crossings of the transient signal associated with a first threshold value, and said second digital waveform representing cycle crossings of the transient signal associated with a second threshold value, said first and second threshold value being less than or equal to an initial amplitude value of the transient signal received;
(b) determining a first total cycles of said first digital waveform and determining a second total cycles of said second digital waveform;
(c) generating the frequency response dataset to comprise total-cycle values counted as a function of frequency, such that each said total-cycle value comprises one of said first and second total cycles; and
(d) having selected the resonator-type sensor element from the group of sensor elements consisting of magnetoelastic elements, quartz crystal microbalance (QCM) elements, and piezoelectric acoustic wave elements.

31. The method of claim 30 wherein each said total-cycle value is a sum of at least said first and second total cycles counted.

32. The method of claim 30 further comprising the steps of:
(a) converting the transient signal received into a third digital waveform representing cycle crossing of the transient signal associated with a third threshold value; and
(b) determining a third total cycles of said third digital waveform; wherein each said total-cycle value is a sum of at least said first, second, and third total cycles counted.

33. The method of claim 30 further comprising the steps of:
(a) generating a second frequency response dataset for a second transient signal received, having been emitted from a second resonator type sensor element said second frequency response dataset to comprise second total-cycle values counted as a function of frequency;
(b) generating a third frequency response dataset for a third transient signal received, having been emitted from a third resonator-type sensor element, said third frequency response dataset to comprise third total-cycle values counted as a function of frequency; and
(c) for each said frequency response dataset so generated, identify a respectively resonant frequency for each said respective first, second, and third sensor element by identifying a peak-value for each said respective frequency response dataset.

34. A method for generating a frequency response dataset for a transient signal received, having been emitted from a resonator-type sensor element, the method comprising the steps of:
(a) converting the transient signal received into a first, second, and third digital waveform; said first digital waveform representing cycle crossings of the transient signal associated with a first threshold value, said second digital waveform representing cycle crossing of the transient signal associated with a second threshold value, and said third digital waveform representing cycle crossings of the transient signal associated with a third threshold value, said first, second, and third threshold value being less than or equal to an initial amplitude value of the transient signal received;
(b) determining a first total cycles of said first digital waveform, determining a second total cycles of said second digital waveform, and determining a third total cycles of said third digital waveform;
(c) generating the frequency response dataset to comprise total-cycle values counted as a function of frequency, such that each said total-cycle value is a sum of at least said first, second, and third total cycles counted; and
(d) the resonator-type sensor element having been selected from the group of sensor elements consisting of magnetoelastic elements.

* * * * *